United States Patent
Manoharan et al.

(10) Patent No.: US 6,653,458 B1
(45) Date of Patent: Nov. 25, 2003

(54) MODIFIED OLIGONUCLEOTIDES

(75) Inventors: Muthiah Manoharan, Carlsbad, CA (US); Phillip Dan Cook, Fallbrook, CA (US); Charles J. Guinosso, Vista, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/435,806

(22) Filed: Nov. 8, 1999

Related U.S. Application Data

(63) Continuation-in-part of application No. 09/115,043, filed on Jul. 14, 1998, now abandoned, and a continuation-in-part of application No. 08/602,862, filed on Feb. 28, 1996, and a continuation-in-part of application No. PCT/US94/10131, filed on Sep. 2, 1994, and a continuation-in-part of application No. 08/117,363, filed on Sep. 3, 1993.

(51) Int. Cl.[7] .................. C07H 19/00; C07H 21/00; C07H 21/02; C07H 21/04
(52) U.S. Cl. .................. 536/23.1; 536/22.1; 536/25.3; 536/25.31; 536/25.32; 536/25.33; 536/25.34
(58) Field of Search .................. 536/22.1, 23.1, 536/25.3, 25.31, 25.32, 25.33, 25.34

(56) References Cited

U.S. PATENT DOCUMENTS

| | | | |
|---|---|---|---|
| 3,687,808 A | 8/1972 | Merigan et al. ............. 195/28 |
| 4,381,344 A | 4/1983 | Rideout et al. ............. 435/87 |
| 4,515,781 A | 5/1985 | Torrence et al. ............. 514/46 |
| 4,689,320 A | 8/1987 | Kaji ............. 514/44 |
| 4,743,535 A | 5/1988 | Carrico ............. 435/6 |
| 4,910,300 A | 3/1990 | Urdea et al. ............. 536/287 |
| 4,959,463 A | 9/1990 | Froehler et al. ............. 536/27 |
| 5,015,733 A | 5/1991 | Smith et al. ............. 536/23 |
| 5,108,921 A | 4/1992 | Low et al. ............. 435/240.1 |
| 5,138,045 A | 8/1992 | Cook et al. ............. 536/27 |
| 5,188,897 A * | 2/1993 | Suhadolnick et al. ............. 428/402.2 |
| 5,212,295 A | 5/1993 | Cook ............. 536/26.7 |
| 5,378,825 A | 1/1995 | Cook et al. ............. 536/25.34 |
| 5,405,939 A | 4/1995 | Suhadolnik et al. ............. 530/322 |
| 5,434,257 A * | 7/1995 | Matteucci et al. ............. 536/24.3 |
| 5,466,786 A | 11/1995 | Buhr et al. ............. 536/26.26 |
| 5,470,967 A | 11/1995 | Huie et al. ............. 536/24.3 |
| 5,532,130 A | 7/1996 | Alul ............. 435/6 |
| 5,550,111 A | 8/1996 | Suhadolnik et al. ............. 514/44 |
| 5,571,799 A | 11/1996 | Tkachuk et al. ............. 514/47 |
| 5,578,718 A | 11/1996 | Cook et al. ............. 536/27.21 |
| 5,817,781 A * | 10/1998 | Swaminathan et al. ............. 536/22.1 |

FOREIGN PATENT DOCUMENTS

| | | |
|---|---|---|
| EP | 0 251 283 | 6/1987 |
| WO | WO 86/02929 | 5/1986 |
| WO | WO 89/02931 | 4/1989 |
| WO | WO 89/12060 | 12/1989 |
| WO | WO 90/10448 | 9/1990 |
| WO | WO 91/00243 | 1/1991 |
| WO | WO 91/14696 | 10/1991 |
| WO | WO 91/15500 | 10/1991 |
| WO | WO 92/05186 | 4/1992 |

OTHER PUBLICATIONS

Manoharan et al. "2'–O– and 3'–O–pyrimidine aminoether–conatining oligonucleotides: synthesis and conjugation chemistry" Tetrahedron Letters, Vol 36, No. 21, pp. 3647–3650, 1995.*

(List continued on next page.)

*Primary Examiner*—Jezia Riley
(74) *Attorney, Agent, or Firm*—Woodcock Washburn LLP

(57) ABSTRACT

Modified oligonucleotides containing at least one 2',5'-internucleotide linkage are provided. The oligonucleotides of the invention may also bear additional substituents at the 2'- and 3'-positions.

16 Claims, 4 Drawing Sheets

OTHER PUBLICATIONS

Dean, N.M. et al., "Inhibition of protein kinase C–α expression in mice after systemic administration of phosphorthioate antisense oligodeoxynuleotides", *Proc. Natl. Acad. Sci.,* 1994, 91, 11762–11766.

Dougherty et al., "Oligodeoxynucleotides That Contain 2',5" Linkages: Synthesis and Hybridization Properties", *J. Am. Chem. Soc.,* 1992, 114, 6254–6256.

Freier, S.M. et al., "The ups and downs of nucleic acid duplex stability: structure–stability studies on chemically–modified DNA:RNA duplexes", *Nucl. Acids Res.,* 1997, 25, 4429–4443.

Giannaris et al., "Oligoribonucleotides containing 2',5'-phosphodiester linkages exhibit binding selectively for 3',5'-RNA over 3',5'-ssDNA", *Nucl. Acids Res.,* 1993, 21(20), 4742–4749.

Griffin et al., "In Vivo Anticoagulant Properties of a Novel Nucleotide-Based Thrombin Inhibitor and Demonstration of Regional Anticoagulation in Extracorporeal Circuits", *Blood,* 1993, 81(12), 3271–3276.

Imai, J. et al., "Chemical Modification Potentiates the Biological Activities of 2–5A and its Congeners", *J. Biol. Chem.,* 1982, 25(21), 12739–12745.

Kabanov, A.V., "A new class of antivirals: antisense olgonucleotides combined with a hydrophobic substituent effectively inhibit influenza virus reproduction and synthesis of virus-specific proteins in MDCK cells", *FEBS Letts.,* 1990, 259, 327–330.

Kandimalla et al., "Mixed backbone antisense oligonucleotides: design, biochemical and biological properties of oligonucleotides containing 2'-5'-ribo–and 3'-5'-deoxyribonucleotide segments", *Nucl. Acids Res.,* 1997, 25(2), 370–378.

Kovacs et al., "Solid Phase Synthesis of 2',5'-Oligoadenylates Containing 3'-Fluorinated Ribose", *Nucleosides and Nucleotides,* 1995, 14(6), 1259–1267.

Kroschwitz, J.I., "Polynucleotides", *Concise Encyclopedia of Polymer Science and Engineering,* 1990, John Wiley & Sons, New York, 858–859.

Lesiak et al., "2',5'-Oligoadenylate: Antisense Chimeras—Synthesis and Properties", *Bioconjugate Chem.,* 1993, 4, 467–472.

Manoharan, M. et al., "Introduction of a Lipophilic Thioether Tether in the Minor Groove of Nucleic Acids for Antisense Applications", *Bioorg. Med. Chem. Letts.,* 1993, 3, 2765–2770.

Manoharan M. et al., "Oligonucleotide Conjugates: Alteration of the Pharmacokinetic Properties of Antisense Agents", *Nucleosides and Nucleotides,* 1995, 14, 969–973.

Manoharan, M. et al., "Lipidic Nucleic Acids", *Tetrahedron Letts.,* 1995, 36, 3651–3654.

Manoharan M. et al., "Cholic Acid–Oligonucliotide Conjugates for Antisense Applications", *Bioorganic Med. Chem. Letts.,* 1994, 4, 1053–1060.

Milligan et al., "Current Concepts in Antisense Drug Design", *J. Med. Chem.,* 1993, 36(14), 1923–1937.

Mishra, R.K. et al., "Improved leishmanicidal effect of phosphorotioate antisense oligonucleotides by LDL–medicated delivery", *Biochim. Et Biophysica,* 1995, 1264, 229–237.

Monia et al., "Sequence-specific antitumor activity of a phosphorothioate oligodeoxyribonucleotide targeted to human C-raf kinase supports an antisense mechanism of action in vivo", *Proc. Natl. Acad. Sci. USA,* 1996, 93, 15481–15484.

Oberhauser, B. et al., "Effective incorporation of 2'-O-methyl-oligonucleotides into liposomes and enhanced cell association through modification with thiocholesterol", *Nucl. Acids Res.,* 1992, 20, 533–538.

Pfleiderer et al., "Synthesis of New Modified 2',5'-Adenylate Trimers Carrying 3'-Amino–3'-Deoxyadenosine at the 2'-Terminus", *Bioorg. Med. Chem. Lett.,* 1994, 4(8), 1047–1052.

Prakash et al., "RNA recognition by the 2'-structural isomer of DNA", *Chem. Commun.,* 1996, 1793–1794.

Prakash et al., "Activity of 2',5'-Linked RNA in the Template-Directed Oligomerization of Mononucleotides", *Angew. Chemie,* 1997, 36, 1522–1523.

Saison-Behmoaras, T. et al., "Short modified antisense oligonucleotides directed against Ha-ras point mutation induce selective cleavage of the mRNA and inhibit T24 cells proliferation", *EMBO J.,* 1991, 10, 1111–1118.

Sanghvi, Y.S., "Heterocyclic Base Modifications in Nucleic acids and their Applications in Antisense Oligonucleotides", *Antisense Research and Applications,* 1993, Chapter 15, CRC Press, Boca Raton, 273–288.

Secrist, J.A. et al., "Synthesis and Biological Activity of 4'-Thionucleosides", *10th International Rountable: Nucleosides, Nucleotides and their Biological Applications,* Sep. 16–20, 1992, Abstract 21, Park City, Utah, 40.

Sheppard et al., "Selective Binding of RNA, but Not DNA, by Complementary 2',5'-Linked DNA", *J. Am. Chem. Soc.,* 1992, 118, 9810–9811.

Silverman, R.H., "Compound that Fights Cancer by Limiting Action of Telomerase to be Featured at Sixth Annual Antisense Conference", Atlantic Pharmaceuticals, Inc., Feb. 3, 1997, 3 pages.

Svinarchuk, F.P. et al., "Inhibition of HIV proliferation in MT-4 cells by antisense oligonucleotide conjugated to lipophilic groups", *Biochimie,* 1993, 79, 49–54.

Wagner et al., "Antisense Gene Inhibition by Oligonucleotides Containing C–5 Propyne Pyrimidines", *Science,* 1993, 260, 1510–1513.

Young et al., "Triple helix formation inhibits transcription elongation in vitro", *Proc. Natl. Acad. Sci.,* 1991, 88, 10023–10026.

Greene et al., *Protective Groups in Organic Synthesis,* 2d edition, New York: John Wiley & Sons, 1991.

Asseline, U. et al., "Solid-Phase Preparation of 5',3'-Heterobifunctional Oligodeoxynucleotides using Modified Solid Supports", *Tetrahedron,* 1992, 48, 1233–1254.

Baker, B.F., "'Decapitation' of a 5'-Capped Oligoribonucleotide by σ-Phenanthroline: Cu(II)", *J. Am. Chem. Soc.,* 1993, 115, 3378–3379.

Bennett, C.F. et al., "Cationic Lipids Enhance Cellular Uptake and Activity of Phosphorothioate Antisense Oligonucleotides", *Mol. Pharmacol.,* 1992, 41, 1023–1033.

Bischoff, R. et al., "Introduction of 5'-Terminal Functional Groups into Synthetic Oligonucleotides for selective Immobilization", *Analyt. Biochem.,* 1987, 164, 336–344.

Blackburn, G.M. et al., "Studies in Phosphorylation. Part XXIX. The Synthesis of Dialkyl Phosphates from Monoalkyl Phosphonates: Direct Oxidative Esterification", *J. Chem. Soc.,* 1966, 239–245.

Caruthers, M.H., "Synthesis of Oligonucleotides and Oligonucleotide Analogues", *Oligonucleotides: Antisense Inhibitors of Gene Expression,* 1989, Chapter 1, Cohen, J.S. (Ed.), CRC Press, Boca Raton, FL, 7–24.

Chiang, M.Y. et al., "Antisense Oligonucleotides Inhibit Intercellular Adhesion Molecule 1 Expression by Two Distinct Mechanisms", *J. Biol. Chem.,* 1991, 266, 18162–18171.

Dingwall, C. et al., "Protein Import into the Cell Nucleus", *Ann. Rev. Cell Biol.,* 1986, 2, 367–390.

Di Zio, J.P. et al., "Progestin–Rhenium Complexes: Metal–Labeled Steroids with High Receptor Binding Affinity, Potential Receptor–Directed Agents for Diagnostic Imaging or Therapy", *Biconjugate Chem.,* 1991, 2, 353–366.

Egholm, M. et al., "Peptide Nucleic Acids (PNA). Oligonucleotide Analogues with an Achiral Peptide Backbone", *J. Am. Chem Soc.,* 1992, 114, 1895–1897.

Ferentz, A.E. et al., "Disulfide Cross–Linked Oligonucleotides", *J. Am. Chem. Soc.,* 1991, 113, 4000–4002.

Fidanza, J.A. et al., "Site–Specific Labeling of DNA Sequences Containing Phosphorothioate Diesters", *J. Am. Chem. Soc.,* 1992, 114, 5509–5517.

Fidanza, J.A. et al., "Use of a Thiol Tether for the Site–Specific Attachment of Reporter Groups to DNA", *J. Org. Chem.,* 1992, 57, 2340–2346.

Froehler, B.C. et al., "Synthesis of DNA via deoxynucleoside II–phosphate intermediates", *Nucl. Acids Res.,* 1986, 14, 5397–5407.

Gaur, R.K. et al., "A simple method for the introduction of a thiol group at 5'–termini of oligodeocynucleotides", *Nucl. Acids Res.,* 1989, 17, 4404.

Greenfield, L. et al., "Thiol–Containign Cross–Linking Agent with Enhanced Steric Hindrance", *Bioconjugate Chem.,* 1990, 1, 400–410.

Harris, C.M. et al., "New Strategy for the Synthesis of Oligodeoxynucleotides Bearing Adducts at Exocyclic Amino Sites of Purine Nucleosides", *J. Am. Chem. Soc.,* 1991, 113, 4328–4329.

Jablonski, E. et al., "Preparation of oligodeoxynucleotide—alkaline phosphatase conjugates and their use as hybridization probes", *Nucl. Acids Res.,* 1986, 14, 6115–6128.

MacMillan, A.M. et al., "Synthesis of Functionally Tethered Oligodeoxynucleotides by the Convertible Nucleoside Approach", *J. Org. Chem.,* 1990, 55, 5931–5933.

Meyer, R.B. et al., "Efficient, Specific Cross–Linking and Cleavage of DNA by Stable, Synthetic Complementary Oligodeoxynucleotides", *J. Am. Chem. Soc.,* 1989, 111, 8517–8519.

Mirabelli, C.K. et al., "In vitro and in vivo pharmacologic activities of antisense oligonucleotides", *Anti–Cancer Drug Des.,* 1991, 6, 647–661.

Mitchell, M.J. et al., "Boron trifluoride–methanol complex as a non–depurinating detritylating agent in DNA Synthesis", *Nucl. Acids Res.,* 1990, 18, 5321.

Mori, K. et al., "Synthesis and Properties of Novel 5'–Linked Oligos", *Nucleosides & Nucleotides,* 1989, 8, 649–657.

Pidgeon, C. et al., "Synthesis and Liposome Encapsulation of Antisense Oligonucleotide–Intercalator Conjugates", *Annals NY Acad. Sci.,* 593–596.

Schwartz, A. et al., "The DNA Bending by Acetylaminofluorene Residues and by Apurinic Sites", *J. Mol. Biol.,* 1989, 207, 445–450.

Sigman, D.S. et al., "Chemical Nucleases", *Biochem.,* 1990, 29, 9097–9105.

Sinha, N.D. et al., "The preparation and application of functionalised synthetic oligonucleotides: III. Use of H–phosphonate derivatives of protected amino–hexanol and mercapto–propanol or –hexanol", *Nucl. Acids. Res.,* 1988, 16, 2659–2669.

Sluka, J.P. et al., "Reagents and Methods for the Solid–Phase Synthesis of Protein–EDTA for Use in Affinity Cleaving", *J. Am. Chem. Soc.,* 1990, 112, 6369–6374.

Sproat, B.S. et al., "The synthesis of protected 5'–mercapto–2', 5'–dideoxyribonucleoside–3'–O–phosphoramidites; users of 5'–mercapto–oligodeoxyribonucleotides", *Nucl. Acids Res.,* 1987, 15, 4837–4849.

Tseng, B.Y. et al., "Antisense oligocucleotide technology in the development of cancer therapeutics", *Cancer Gene Therapeutics,* 1994, 1, 65–71.

Uhlmann, E. et al., "Antisense Oligonucleotides: A New Therapeutic Principle", *Chem. Reviews,* 1990, 90, 544–584.

Vasseur, J.J. et al., "Oligonucleosides: Synthesis of a Novel Methylhydroxylamine–linked Nucleoside Dimer and Its Incorporation into Antisense Sequences", *J. Am. Chem. Soc.,* 1992, 114, 4006–4007.

Wychowski, C. et al., "The Intranuclear Location of Simian Virus 40 Polypeptides VP2 and VP3 Depends on a Specific Amino Acid Sequence", *J. Virology,* 1987, 61, 3862–3869.

Yoneda, Y. et al., "Synthetic Peptides Containing a Region of SV40 Large T–Antigen Involved in Nuclear Localization Direct the Transport of Proteins into the Nucleus", *Exp. Cell Res.,* 1987, 170, 439–452.

Zhang, Z. et al., "Uptake of N–(4'–pyridoxyl)amines and release of amines by renal cells: A model for transporter–enhanced delivery of bioactive compounds", *Proc. Natl. Acad. Sci.,* 1991, 88, 10407–10410.

Zuckermann, R. et al., "Efficient methods for attachment of thiol specific probes to the 3'–ends of synthetic oligodeoxyribonucleotides", *Nucl. Acids Res.,* 1987, 15, 5305–5321.

Agarwal, K.L. et al., "Synthesis and enzymatic properties of deoxyribooligonucleotides containing methyl and phenylphosphonate linkages," *Nucl Acids Res.,* 1979, 6, 3009–3023.

Agris, C.H. et al., "Inhibition of Vesicular Stomatitis Virus Protein Synthesis and Infection by Sequence–Specivid Oligodeoxyribonucleoside Methylphosphonates", *Biochem.,* 1986, 25, 6268–6275.

Castle, R.N. et al., "Imidazo[4,5–d] pyridazines. I. Synthesis of 4,7–Disubstituted Derivatives", *J. Org. Chem.,* 1958, 23, 1534–1538.

Hobbs, J. et al., "Polynucleotides Containing 2'–Chloro–2'–deoxyribose", *Biochem.,* 1972, 11, 4336–4344.

Jager, A. et al., "Oligonucleotide N–Alkylphosphoramidates: Synthesis and Binding to Polynucleotides", *Biochem.,* 1988, 27, 7237–7246.

Jayaraman, K. et al., "Selective Inhibition of *Escherichia coli* protein synthesis and growth by nonionic olignucleotides complementary to the 3' end of 16S rRNA", *Proc. Natl. Acad. Sci.,* 1981, 78, 1537–1541.

Jones, G.H. et al., "4'–Substituted Nucleosides. 5. Hydroxymethylation of Nucleoside 5'–Aldehydes", *J. Org. Chem.,* 1979, 44, 1309–1317.

Kazimierczuk, Z. et al., "Synthesis of 2'–Deoxytubercidin, 2'–Deoxyadenosine, and Related 2'–Deoxynucleosides via Novel Direct Stereospecific Sodium Salt Glycosylation Procedure", *J. Am. Chem. Soc.,* 1984, 106, 6379–6382.

Knorre, D.G. et al., "Complemetary–Addressed (Sequence–Specific) Modification of Nucleic Acids", 1985, 32, 291–321.

Le Doan, T. et al., "Sequence–targeted chemical modification of nucleic acids by complementary oligonucleotides covalently linked to porphyrins", *Nucl. Acids Res.,* 1987, 15, 8643–8659.

Letsinger, R.L. et al., "Effects of pendant groups at phosphorus on binding properties of d–ApA analogues", *Nuc. Acids. Res.,* 1986, 14, 3487–3498.

Loose–Mitchell, D.S., "Antisense nucleic acids as a potential class of pharmaceutical agents", *TiPS,* 1996, 9, 45–47.

Marcus–Sekura, C.J. et al., "Comparative inhibition of chloramphenicol acetyltransferase gene expression by antisense oligonucleotide analogues having alkyl phosphotriester, methylphosphonate and phosphorothioate linkages", *Nucl. Acids Res.,* 1987, 15, 5749–5763.

Matsukura, M. et al., "Phosphorothioate analogs of oligodeoxynucleotides: Inhibitors of replication and cytopathic effects of human immunodeficiency virus", *Proc. Natl. Acad. Sci.,* 1987, 84, 7706–7710.

Miller, P.S. et al., "Synthesis and Properties of Adenine and Thymine Nucleoside Alkyl Phosphotriesters, the Neutral Analogs of Dinucleoside Monophosphates", *J. Am. Chem. Soc.,* 1971, 93, 6657–6664.

Miller, P.S. et al., "Nonionic Nucleic Acid Analogues. Synthesis and Characterization of Dideoxyribonucleoside Methylphosphonates", *Biochem.,* 1979, 18, 5134–5143.

Miller, P.S. et al., "Biochemical and Biological Effects of Nonionic Nucleic Acid Methylphosphonates", *Biochem.,* 1981, 20, 1874–1880.

Outten, R.A. et al., "Synthetic 1–Methoxybenzo[d]naphtho [1,2–b]pyran–6–one C–Glycosides", *J. Org. Chem.,* 1987, 52, 5064–5066.

Robins, M.J. et al., "Nucleic Acid Related Compounds. 42. A General Procedure for the Efficient Deoxygenation of Secondary Alcohols. Regiospecific and Stereoselective Conversion of Ribonucleosides to 2'–Deoxynucleosides", *J. Am. Chem. Soc.,* 1983, 105, 4059–4065.

Roelen, H.C.P.F. et al., "Synthesis of nucleic acid methylphosphonthioates", *Nucl. Acids Res.,* 1988, 16(15), 7633–7645.

Ruby, S.W. et al., "An Early Hierarchic Role of U1 Small Nuclear Ribonucleoprotein in Spliceosome Assembly", *Science,* 1988, 242, 1028–1035.

Shibahara, S. et al., "Inhibition of human immunodeficiency virus (HIV–1) replication by synthetic oligo–RNA derivatives," 1989, 17(1), 239–252.

Sigman, D.S. et al., "Nuclease Activity of 1,10–Phenanthroline–Copper Ion", *Acc. Chem. Res.,* 1986, 19, 180–186.

Smith, C.C. et al., "Antiviral effect of an oligo(nucleoside methylphosphonate) complementary to the splice junction of herpes simplex virus type 1 immdiate early re–mRNAs 4 and 5", *Proc. Natl. Acad. Sci.,* 1986, 83, 2787–2791.

Stein, C.A. et al., "Oligodeoxynucleotides as Inhibitors of Gene Expression: A Review", *Cancer Res.,* 1988, 48, 2659–2668.

Stein, C.A. et al., "Physiochemical proterties of phosphorothioate oligodeoxynucleotides", *Nucl. Acids Res.,* 1988, 16, 3209–3221.

Suciu, N. et al., "Synthesis of 9–(2,5dideoxy–β–D–glycero–pent–3–enofuranosyl)adenine", *Carbohydrate Res.,* 1975, 44, 112–115.

Tibanyenda, N. et al., "The effect of single base–pair mismatches on the duplex stability of d(T–A–T–T–A–A–T–A–T–C–A–A–G–T–T–G) d(C–A–A–C–T–T–G–A–T–A–T–T–A–A–T–A)", *Eur. J. Biochem.,* 1984, 139, 19–27.

Tidd, D.M. et al., "Evaluationof N–ras oncogene antisense, sense, and nonsense sequence methylphosphonate oliconucleotide analogues", *Anti–Cancer Drug Design,* 1988, 3, 117–127.

Uesugi, S. et al., "A Linear Relationship Between Electronegativity of 2'–Substituents and Conformation of Adenine Nucleosides", *Tetrahedron Letts.,* 1979, 42, 4073–4076.

van der Krol, A.R. et al., "Modulation of Eukaryotic Gene Expression by Complementary RNA or DNA Sequences", *BioTechniques,* 1988, 6, 958–976.

Walder, R. et al., "Role and RNase H in hybrid–arrested translation by antisense oligonucleotides", *Proc. Natl. Acad. Sci.,* 1988, 85, 5011–5015.

Yeung, A.T. et al., "Photoreactivities and Thermal Properties of Psoralen Cross–Links", *Biochemistry,* 1988, 27, 3204–3210.

Butke, G. et al., "Facile Synthesis of 2'–Amino–2'Deoxyadenosine", *J. Carbohydrates, Nucleosides, Nucleotides,* 1980, 7, 63–75.

Calvo–Mateo, A. et al., "3'–C–Cyano–3'–Deoxythymidine", *Tetrahedron Letts.,* 1988, 23, 941–944.

Codington, J.F. et al., "Nucleosides. XVIII. Synthesis of 2'–Fluorothymidine, 2'–Fluorodeoxyuridine, and Other 2'–Halogeno–2'–Deoxy Nucleosides", *J. Org. Chem.,* 1964, 29, 558–564.

Damha, M.J. et al., "Solution and solid phase chemical synthesis of arabinonucleotides", *Can. J. Chem.,* 1989, 67, 831–839.

Ikehara, M. et al., "Studies of Nucleosides–and Nucleotides–LXXXII. Cyclonucleosides. (39). Synthesis and Properties of 2'–Halogeno–2'–deoxyadenosines", *Chem. Pharm. Bull.,* 1978, 26, 2449–2453.

Ikehara, M. et al., "Purine Cyclonucleosides–26 A Versatile Method for the Synthesis of Purine O–Cyclo—Nucleosides", *Tetrahedron,* 1975, 31, 1369–1372.

Ikehara, M., "Purine 8–Cyclonucleosides", *Accts. Chem. Res.,* 1969, 2, 47–53.

Ikehara, M. et al., "Studies of Nucleosides–and Nucleotides—LXXXIX. Purine Cyclonucleosides. (43). Synthesis and Properties of 2'–Halogeno–2'–deoxyguanosines", *Chem. Pharm. Bull.,* 1981, 29, 3281–3285.

Jarvi, E.T. et al., "Synthesis and Biological Evaluation of Dideoxynucleosides Containing a Difluoromethylene Unit", *Nucleosides & Nucleotides,* 1989, 8, 1111–1114.

Koole, L.H. et al., "Synthesis of Phosphate–Methylated DNA Fragments Using 9–Fluoroenylmethoxycarbonyl as Transient Base Protecting Group", *J. Org. Chem.,* 1989, 54, 1657–1664.

Markiewicz, W.T. et al., *Nucl. Acid Chem.,* 1986, Part 3, 222–231.

Parkes, K.E.B. et al., "A Short Synthesis of 3'–Cyano–3'–Deoxythymidine", *TetrahedronLetts.,* 1988, 29, 2995–2996.

Ranganathan, R., "Modification of the 2'–Position of Purine Nucleosides: Synthesis of 2'–α–Substituted–2'–deoxyadenosine Analogs", *Tetrahedron Letts.,* 1977, 15, 1291–1294.

Sproat, B.S. et al., "Highly efficient chemical synthesis of 2'-O-methyloligoribonucleotides and tetrabiotinylated derrivatives; novel proobes that are resistant to degradation by RNA or DNA specific nucleases", *Nucl. Acids Res.,* 1989, 17, 3373–3386.

Sproat, B.S. et al., "New synthetic routes to protected purine 2-O-methylriboside-3'-O-phosphoramidites using a novel alkylation procedure", *Nucl. Acids Res.,* 1990, 18, 41–49.

Ti, G.S. et al., "Transient Protection: Efficient One-Flask Synthesis of Protected Deoxynucleosides", *J. Am. Chem. Soc.,* 1982, 104, 1316–1319.

Uesugi, S. et al., "Improved Synthesis of 2'-Fluoro-2'-Deoxyadenosine and Synthesis and Carbon-13 NMR Spectrum of its 3',5'-Cyclic Phosphate Derivative", *Nuclecosides & Nucleotides,* 1983, 2, 373–385.

Gaffney et al., "A New Strategy for the Protection of Deoxyguanosine During Oligonucleotide Synthesis", *Tetra. Lett.,* 1982, 23, 2257–2260.

Seela et al., "Palindromic Octa– and Dodecanucleotides Containing 2'-Deoxytubercidin: Synthesis, Hairpin Formation, and Recognition by the Endodeoxyribonuclease EcoRI" *Biochem.,* 1987, 26, 22333–2238.

Alul et al., "(2'-5')-Oligo-3'-Deoxynucleotides: Selective Binding to Single–Stranded RNA but Not DNA", *Antisense Res. Dev.,* 1995, 5, 3–11.

Bayard, B. et al., "Activation of Ribonuclease L by (2'-5')(A) $^4$-Poly(L-lysine) Conjugates in Intact Cells", *Biochem.,* 1986, 25, 3730–3736.

Beal et al., "Second Structural Motif for Recognition of DNA by Oligonucleotide–Directed Triple–Helix Formation", *Science,* 1991, 251, 1360–1363.

Beaucage, S.L. et al., "Advances in the Synthesis of Oligonucleotides by the Phosphoramidite Approach", *Tetrahedron,* 1992, 48, 2223–2311.

Bhan, P. et al., "Inhibition of 5–α–Reductase (Type–II) Expression by Antisense 3'–Deoxy–2(2'–5') Oligonucleotide Chimeras", *Nucleosides and Nucleotides,* 1997, 16(7–9), 1195–1199.

Bock et al., "Selection of single–stranded DNA molecules that bind and inhibit human thrombin", *Nature,* 1992, 355, 564–566.

Cook, P.D., "Medicinal chemistry of antisense oligonucleotides—future opportunities", *Anti–Cancer Drug Design,* 1991, 6, 585–607.

Crooke, S.T. et al., "Pharmacokinetic Properties fo Several Novel Oligonucleotide Analogs in mice", *J. Pharmacol. Exp. Therapeutics,* 1996, 277, 923–937.

Damha, M.J. et al., "An improved procedure for derivatization of controlled–pore glass beads for solid–phase oligonucleotide synthesis", *Nucl. Acids Res.,* 1990, 18, 3813–3821.

* cited by examiner

MODIFIED OLIGONUCLEOTIDES

CROSS REFERENCE TO RELATED APPLICATIONS

This application is a continuation in part of U.S. Ser. No. 09/115,043, filed Jul. 14, 1998 now abandoned; a continuation in part of U.S. Ser. No. 08/602,862, filed Feb. 28, 1996; a continuation in part of international patent application Ser. No. PCT/US94/10131, filed Sep. 2, 1994; and a continuation in part of U.S. Ser. No. 08/117,363, filed Sep. 3, 1993. The contents of each of the foregoing applications are incorporated by reference herein in their entireties.

FIELD OF THE INVENTION

This invention is directed to modified oligonucleotides that include one or more 2'-5' internucleotide linkages and a modified nucleotide at one of the two nucleotides that are linked by the 2',5' linkage. That nucleotide is modified, for example, by incorporating a substituent at its 3'-position. The modified oligonucleotides of the present invention exhibit improved properties of nuclease resistance and binding affinity, and are of use as antisense oligonucleotides.

BACKGROUND OF THE INVENTION

It is well known that most of the bodily states in mammals, including most disease states, are affected by proteins. Classical therapeutic modes have generally focused on interactions with such proteins in an effort to moderate their disease-causing or disease-potentiating functions. However, recently, attempts have been made to moderate the actual production of such proteins by interactions with molecules that direct their synthesis, such as intracellular RNA. By interfering with the production of proteins, maximum therapeutic effect and minimal side effects may be realized. It is the general object of such therapeutic approaches to interfere with or otherwise modulate gene expression leading to undesired protein formation.

One method for inhibiting specific gene expression is the use of oligonucleotides. Oligonucleotides are now accepted as therapeutic agents with great promise. Oligonucleotides are known to hybridize to single-stranded DNA or RNA molecules. Hybridization is the sequence-specific base pair hydrogen bonding of nucleobases of the oligonucleotide to the nucleobases of the target DNA or RNA molecule. Such nucleobase pairs are said to be complementary to one another. The concept of inhibiting gene expression through the use of sequence-specific binding of oligonucleotides to target RNA sequences, also known as antisense inhibition, has been demonstrated in a variety of systems, including living cells (for example see: Wagner et al., Science (1993) 260: 1510–1513; Milligan et al., *J. Med. Chem.,* (1993) 36:1923–37; Uhlmann et al., *Chem. Reviews,* (1990) 90:543–584; Stein et al., *Cancer Res.,* (1988) 48:2659–2668).

The events that provide the disruption of the nucleic acid function by antisense oligonucleotides (Cohen in *Oligonucleotides: Antisense Inhibitors of Gene Expression,* (1989) CRC Press, Inc., Boca Raton, Fla.) are thought to be of two types. The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides: Miller, P. S. and Ts'O, P.O.P. (1987) *Anti-Cancer Drug Design,* 2:117–128, and α-anomer oligonucleotides are the two most extensively studied antisense agents which are thought to disrupt nucleic acid function by hybridization arrest.

The second type of terminating event for antisense oligonucleotides involves the enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Oligonucleotides may also bind to duplex nucleic acids to form triplex complexes in a sequence specific manner via Hoogsteen base pairing (Beal et al., *Science,* (1991) 251:1360–1363; Young et al., *Proc. Natl. Acad. Sci.* (1991) 88:10023–10026). Both antisense and triple helix therapeutic strategies are directed towards nucleic acid sequences that are involved in or responsible for establishing or maintaining disease conditions. Such target nucleic acid sequences may be found in the genomes of pathogenic organisms including bacteria, yeasts, fungi, protozoa, parasites, viruses, or may be endogenous in nature. By hybridizing to and modifying the expression of a gene important for the establishment, maintenance or elimination of a disease condition, the corresponding condition may be cured, prevented or ameliorated.

In determining the extent of hybridization of an oligonucleotide to a complementary nucleic acid, the relative ability of an oligonucleotide to bind to the complementary nucleic acid may be compared by determining the melting temperature of a particular hybridization complex. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

Oligonucleotides may also be of therapeutic value when they bind to non-nucleic acid biomolecules such as intracellular or extracellular polypeptides, proteins, or enzymes. Such oligonucleotides are often referred to as 'aptamers' and they typically bind to and interfere with the function of protein targets (Griffin, et al., *Blood,* (1993), 81:3271–3276; Bock, et al., *Nature,* (1992) 355: 564–566).

Oligonucleotides and their analogs have been developed and used for diagnostic purposes, therapeutic applications and as research reagents. For use as therapeutics, oligonucleotides must be transported across cell membranes or be taken up by cells, and appropriately hybridize to target DNA or RNA. These critical functions depend on the initial stability of the oligonucleotides toward nuclease degradation. A serious deficiency of unmodified oligonucleotides which affects their hybridization potential with target DNA or RNA for therapeutic purposes is the enzymatic degradation of administered oligonucleotides by a variety of intracellular and extracellular ubiquitous nucleolytic enzymes referred to as nucleases. For oligonucleotides to be useful as therapeutics or diagnostics, the oligonucleotides should demonstrate enhanced binding affinity to complementary target nucleic acids, and preferably be reasonably stable to nucleases and resist degradation. For a non-cellular use such as a research reagent, oligonucleotides need not necessarily possess nuclease stability.

A number of chemical modifications have been introduced into oligonucleotides to increase their binding affinity to target DNA or RNA and resist nuclease degradation.

Modifications have been made to the ribose phosphate backbone to increase the resistance to nucleases. These modifications include use of linkages such as methyl phosphonates, phosphorothioates and phosphorodithioates, and the use of modified sugar moieties such as 2'-O-alkyl ribose. Other oligonucleotide modifications include those made to modulate uptake and cellular distribution. A number of modifications that dramatically alter the nature of the internucleotide linkage have also been reported in the literature. These include non-phosphorus linkages, peptide nucleic acids (PNA's) and 2'-5' linkages. Another modification to oligonucleotides, usually for diagnostic and research applications, is labeling with non-isotopic labels, e.g., fluorescein, biotin, digoxigenin, alkaline phosphatase, or other reporter molecules.

A variety of modified phosphorus-containing linkages have been studied as replacements for the natural, readily cleaved phosphodiester linkage in oligonucleotides. In general, most of them, such as the phosphorothioate, phosphoramidates, phosphonates and phosphorodithioates all result in oligonucleotides with reduced binding to complementary targets and decreased hybrid stability. In order to make effective therapeutics therefore this binding and hybrid stability of antisense oligonucleotides needs to be improved.

In an effort to study the influence of structural modifications of oligonucleotides on the stability of their duplexes with target RNA, a series of oligonucleotides containing more than 200 different modifications were synthesized and assessed for their hybridization affinity and $T_m$ (Freier and Altmann, *Nucleic Acids Research,* (1997) 25:4429–4443). Sugar modifications studied included substitutions on the 2'-position of the sugar, 3'-b-substitution, replacement of the 4'-oxygen, the use of bicyclic sugars, and four member ring replacements. Several nucleobase modifications were also studied including substitutions at the 5, or 6 position of thymine, modifications of pyrimidine heterocycle and modifications of the purine heterocycle. Numerous backbone modifications were also investigated including backbones bearing phosphorus and those that did not bear a phosphorus atom, and backbones that were neutral. Based on the study of this large set of modified oligonucleotides four general approaches that may be used to improve hybridization of oligonucleotides to RNA targets were identified. These include: preorganization of the sugars and phosphates of the oligodeoxynucleotide strand into conformations favorable for hybrid formation, improved stacking of nucleobases as observed when polarizable groups are added to the heterocycle enhances binding affinity, increasing the number of H-bonds available for A-U pairing also helps binding, and neutralization of backbone charge will also facilitate the biding interactions by removing undesirable repulsive interactions (Freier and Altmann, *Nucleic Acids Research,* (1997) 25:4429–4443).

Sugars in DNA:RNA hybrid duplexes frequently adopt a C3' endo conformation. Thus modifications that shift the conformational equilibrium of the sugar moieties in the single strand toward this conformation should preorganize the antisense strand for binding to RNA. Of the several sugar modifications that have been reported and studied in the literature, the incorporation of electronegative substituents such as 2'-fluoro or 2'-alkoxy shift the sugar conformation towards the northern pucker conformation. This pucker conformation further assisted in increasing the Tm of the oligonucleotide with its target. Large substituents at the 2'-position are, however, not well tolerated. A clear correlation between substituent size at the 2'-position and duplex stability has been observed and reported in the literature. Incorporation of alkyl substituents at the 2'-position typically leads to a significant decrease in binding affinity.

2'-O-alkyl substituents provide a strong positive influence on the binding affinity of oligonucleotides (Freier and Altmann, *Nucleic Acids Research,* (1997) 25:4429–4443). Small alkoxy groups were very favorable, and larger alkoxy groups at the 2'-position were found to be unfavorable. However, if the 2'-substituent contained an ethylene glycol motif, then a strong improvement in binding affinity to the target RNA was observed. This is suggested to arise from gauche interactions between the oxygen g to the 2'-oxygen atom results in a configuration of the side chain that is favorable for duplex formation.

It has been reported that while there are a number of stabilizing modifications to choose from when designing oligonucleotides, the combination of stabilizing features provides the best approach to improving binding affinities. It appears that modified oligonucleotides with very high RNA binding affinity need to be constructed by the combination of two or more different types of modifications, each of which contributes favorably to one of the four general factors important for binding affinity (Freier and Altmann, *Nucleic Acids Research,* (1997) 25:4429–4443).

One type of nucleic acid modification that has seen considerable interest is the 2',5'-oligonucleotides. A number of research groups have revealed the synthesis and study of 2',5'-oligonucleotides and nucleic acids. This modification entails the synthesis of oligonucleotides where the internucleotide linkages are not between the 3' and 5'-positions of the sugars as in natural nucleic acids, but are between the 2' and 5' positions of the sugars of the nucleotide components. The 2',5' internucleotide linkage, and such oligonucleotides, has been under investigation from several different aspects.

2',5/-Oligoadenylates (also referred to as 2-5A) are naturally occurring RNA isomers that are implicated in the regulation of cell growth and in the antiviral mechanism of interferon. Because of the poor uptake of such oligonucleotides and the relatively nonspecific endonucleolytic action of its target RNase L, chimeric oligonucleotides that incorporate 2-5A motifs together with an antisense construct for a specific target have also been studied (Lesiak et al, *Bioconjugate Chem.,* 1993, 4, 467–472). These chimeric oligonucleotides bearing 3'-hydroxy groups at the 2',5'-linkages were found to hybridize to complementary RNA and to activate the 2-5A dependent RNase. 2',5/-Oligoadenylates that bear a fluoro substituent at the 3'-position have been synthesized, via phosphoramidite chemistry, to study the importance and role of the 3'-hydroxy group in the activity of such 2-5A oligonucleotides (Kovacs et al., *Nucleosides and Nucleotides,* 1995, 14, 1259–1267).

2',5/-Oligonucleotides have also been the focus of research aimed at understanding the evolutionary bias towards 3',5' instead of 2',5' linked double helices to encode genetic information (Prakash et al, *Angew. Chemie,* 1997, 36, 1522–23); 2',5' linkages were found to be more susceptible to hydrolysis that their 3',5' analogs. 2',5' phosphodiester linked oligoribonucleotides have also been studied for their binding to RNA and DNA (Giannaris and Damha, *Nucl. Acids Res.*, 1993, 21, 4742–4749). It was found that 2',5' oligoribonucleotides exhibited remarkable selectivity for complementary single stranded RNA over DNA. Further when a 3',5' phosphodiester deoxyribooligonucleotide was altered via replacement of some linkages with 2',5' phosphodiester ribonucleotide linkages, the resulting chimeric oligonucleotide exhibited a lower Tm when binding to both DNA and RNA targets (Giannaris and Damha, *Nucl. Acids Res.*, 1993, 21, 4742–4749, Kandimalla et al, *Nucl. Acids Res.*, 1997, 25, 370–378). This destablization of binding was also found to be related to the number of 2',5' linkages incorporated into the oligonucleotide. Similar mixed backbone oligonucleotide phosphorothioates have also been reported and these show greater destabilization of binding to DNA compared to RNA targets.

During studies on the 2-5A system, 3'-amino analogs of 2-5A trimer oligonucleotide phosphodiesters were synthesized and reported in the literature as exhibiting improved enzymatic stability towards phosphodiesterase (Pfleiderer et al., *Bioorg. Med. Chem. Lett.*, 1994, 4, 1047–1052). These short oligonucleotides were reported to have antiviral effects against HIV in peripheral blood mononuclear cells. Similar 2',5' oligoadenylate analogs have also been synthesized via phosphotriester chemistry and reported to be useful for suppressing the division of T-helper and T-killer cells and for treating autoimmune diseases and the host-vs.-graft response during organ transplant rejection (Tkachuk et al., U.S. Pat. No. 5,571,799, issued Nov. 5, 1996). Several patents also describe 2',5'-oligoadenylate phosphodiesters and phosphorothioates as dual action antiviral agents capable of not only activating the latent RNase L but also inhibiting viral DNA polymerases. These oligonucleotides typically bear no substituent (i.e. are deoxy) or a hydroxyl or amino substituent on the 3'-position of the nucleosides participating in the 2',5' linkage. Conjugates with a variety of molecules and encapsulated formulations have also been described for these 2',5' oligonucleotides (Suhadolnik and Pfleiderer, U.S. Pat. No. 5,188,897, issued Feb. 23, 1993; Suhadolnik and Pfleiderer, U.S. Pat. No. 5,405,939, issued Apr. 11, 1995; Suhadolnik and Pfleiderer, U.S. Pat. No. 5,550,111, issued Aug. 27, 1996).

A number of groups have studied 2',5'-3'-deoxyoligonucleotides. Giannaris and Damha showed that 2',5'-oligoribonucleotides show weaker binding to complementary RNA targets compared to complementary DNA targets (Giannaris and Damha, *Nucl. Acids Res.*, 1993, 21, 4742–4749). Alul and Hoke have reported that 2',5'-oligo-3'-deoxynucleotides exhibit binding similar to that of corresponding 3',5'-oligodeoxynucleotides when studied with a complementary RNA. However, in contrast to most antisense oligodeoxynucleotide analogs, 2',5' oligonucleotides do not bind to complementary DNA. It has also been reported that this change in bond connectivity from 3',5' to 2',5' confers improved resistance to nucleolytic degradation (Alul and Hoke, *Antisense Res. and Dev.*, 1995, 5, 3–11). 2',5/-Oligonucleotide analogs bearing hydroxyl, alkyl, aryl, alkoxy, alkyoxy, aryloxy, and azido substituents at the 3'-position have been claimed in a patent describing methods and compositions for sequence-specific hybridization of RNA (Alul, U.S. Pat. No. 5,532,130, issued Jul. 2, 1996). These oligonucleotides are reported to exhibit greater exo- and endo-nuclease resistance while hybridizing selectively to RNA and not DNA. Chimeric, 21-mer 2',5'-oligo-3'-deoxynucleotide phosphorothioates that contain a short cassette of seven 3',5' linkages in the middle have been reported to be inhibitors of the steroid 5a-reductase in cell culture (Bohn, Hoke and Alul, Proceeding of the Twelfth International Round Table, 1996, in Nucleosides and Nucleotides, 1997, 16, 1195–1179. These chimeric phosphorothioate oligonucleotides bearing both 2',5' and 3',5' linkages exhibited potency similar to the completely 3',5' analogs but with significantly lower non-sequence specific effects.

2',5/-Oligo-3'-deoxynucleotides have also been studied for their binding to RNA and DNA targets and their involvement in prebiotic development and genetic selection. Breslow's group has synthesized 2',5'-linked DNA and studied its binding properties to both RNA and DNA. Selective binding of RNA, but not DNA was observed (Dougherty et al., *J. Am. Chem. Soc.*, 1992, 112, 6254–6255; Sheppard and Breslow, *J. Am. Chem. Soc.*, 1992, 118, 9810–9811). This has been further elaborated to reveal that the duplex formed by 2',5'-DNA with RNA has a stability (Tm) similar to that for the 3',5'-DNA-RNA duplex but that this binding is of a hybrid nature (Prakash et al., *Chem. Commun.*, 1996, 1793–94).

As part of the scientific study of oligonucleotides and antisense oligonucleotides, numerous modifications, besides 2',5' linkages, have been made to the internucleotide linkage. While many of these retain the phosphorus atom present in the natural phosphodiester linkage a number of non-phosphorus linkages have also been studied. One example of these is an unsaturated linkage of four atom chains connecting the two sugar residues of adjacent nucleotide units. Oligonucleotides bearing internucleotide linkages of the type 2'/3'-S—CH2—CH=5'CH2 and 2'/3'-O—CH2—CH=5'CH2 have been reported by Matteucci and Cao (U.S. Pat. No. 5,434,257, issued Jul. 18, 1995). These 2',5' linked oligonucleotides were reported to be stable in vivo, resistant to endogenous nucleases and capable of hybridizing to target nucleic acids.

Of the large number of modifications made and studied, few have progressed far enough through discovery and development to deserve clinical evaluation. Reasons underlying this include difficulty of synthesis, poor binding to target nucleic acids, lack of specificity for the target nucleic acid, poor in vitro and in vivo stability to nucleases, and poor pharmacokinetics. Several phosphorothioate oligonucleotides and derivatives are presently being used as antisense agents in human clinical trials for the treatment of various disease states. Although some improvements in diagnostic and therapeutic uses have been realized with these oligonucleotide modifications, there exists an ongoing demand for improved oligonucleotides that are easy to synthesize, are nuclease resistant and have good binding properties.

The present invention provides modified oligonucleotides that are easy to synthesize and exhibit good properties of nuclease resistance and hybridization to target nucleic acids. This and other objects of the invention will be apparent from a consideration of the specification as a whole.

SUMMARY OF THE INVENTION

The present invention provides oligonucleotides comprising a plurality of nucleotides linked together by internucleotide linkages. Each nucleotide includes a sugar portion and a base portion, and at least one of the internucleotide linkages is a 2',5'-linkage wherein at least one of the linked nucleotides bears a 3'-substituent of the formula:

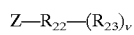

where:

Z is O, S, NH, or N—R$_{22}$—(R$_{23}$)$_v$

R$_{22}$ is C$_1$–C$_{20}$ alkyl, C$_2$–C$_{20}$ alkenyl, or C$_2$–C$_{20}$ alkynyl;

$R_{23}$ is $R_{24}$ when Z is O;

$R_{23}$ is hydrogen or $R_{24}$ when Z is S, NH, or N—$R_{22}$—$(R_{23})_v$;

$R_{24}$ is amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, hydroxyalkyamino, hydroxydialkylamino, disulfide, silyl, aryl, heterocycle, carbocycle, intercalator, reporter molecule, conjugate, polyamine, polyamide, polyalkylene glycol, poly-ether, a group that enhances the pharmacodynamic properties of oligonucleotides, or a group that enhances the pharmacokinetic properties of oligonucleotides;

v is from 0 to about 10.

The present invention further provides oligonucleotides bearing at least one 2',5' internucleotide linkage wherein at least one of the linked nucleotides includes an alkoxyalkoxy, dialkoxyalkoxy, hydroxyalkoxy, dihydroxyalkoxy, aminoalkoxy, alkylaminoalkoxy, dialkylaminoalkoxy, dialkylaminooxyalkoxy, haloalkoxy, dihaloalkoxy or trihaloalkoxy 3'-substituent and protected versions of the same.

In a preferred embodiment, the present invention provides oligonucleotides bearing at the 3'-position a substituent selected from the group consisting of, but not limited to, methoxyethoxy, hydroxyethoxy, dimethylaminooxyethoxy, trifluoromethylethoxy, aminopropoxy, and protected versions of the same.

The present invention also provides oligonucleotides bearing methoxyethoxy substituents at one or more 2'-positions on the sugar portion of the nucleotides.

The present invention further provided oligonucleotide having at least one 2',5' internucleotide linkage wherein at least one of the linked nucleotides includes a 3'-substituent having one of the formulas:

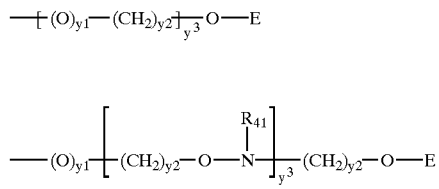

where:

y1 is 0 or 1;

y2 is 0 to 10;

y3 is 1 to 10;

E is $N(R_{41})(R_{42})$ or $N=C(R_{41})(R_{42})$; and each $R_{41}$ and each $R_{42}$ is independently H, $C_1$–$C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heteroatom selected from N and O.

The present invention further provides oligonucleotides comprising a plurality of nucleotides linked together by internucleotide linkages, wherein the linkage is selected from a group consisting of, but not limited to, phosphorus-containing and non-phosphorus-containing linkages. Phosphorus-containing linkages include, but are not limited to, phosphodiester, phosphorothioate, phosphoramidate, alkylphosphonate, N3'->P5' phosphoramidate, phosphinate, phosphate, thiophosphate and phosphorodithioate linkages. Non-phosphorus-containing linkages include, but are not limited to, glycol, ether, all carbon atom, urea, carbamate, amide, cyclic, amine, hydroxylamine, hydrazino, -substituted amide 3, and methylene(methylimino) linkages.

In a preferred embodiment, the internucleotide linkages present in the oligonucleotides of the present invention are either all phosphodiester or all phosphorothioate. In a further preferred embodiment, the internucleotide linkages present in the oligonucleotides of the present invention are any combination of at least one phosphodiester and at least one phosphorothioate linkage.

DETAILED DESCRIPTION OF THE INVENTION

Figure 1:
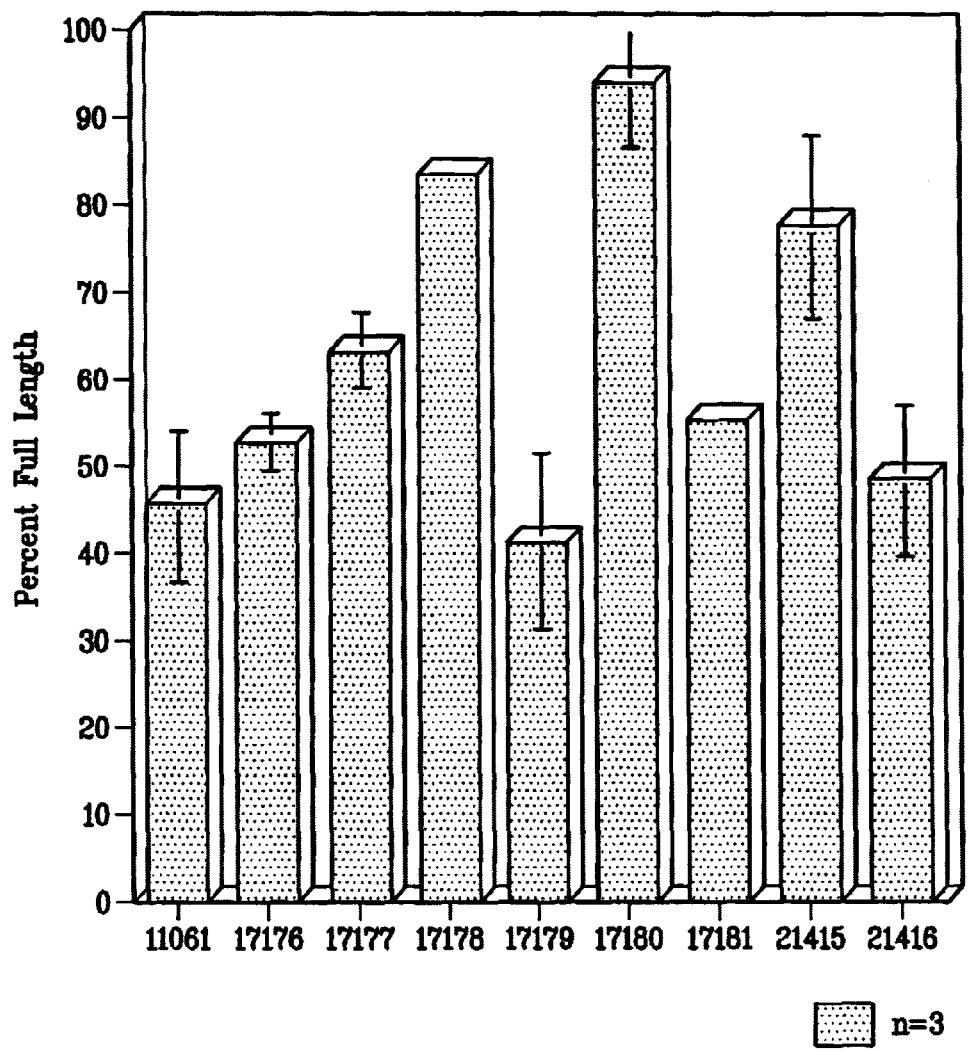
FIG. 1 shows the stability of modified oligonucleotides in mouse plasma 1 h. after i.v. bolus administration.

The present invention provides oligonucleotides comprising a plurality of nucleotides linked together by internucleotide linkages wherein at least one of the internucleotide linkages is a 2',5'-linkage. The nucleotide subunits may be "natural" or "synthetic" moieties. Each nucleotide unit is formed from a naturally occurring or synthetic base portion and a naturally occurring or synthetic pentofuranosyl sugar portion.

The term "oligonucleotide" refers to a polynucleotide formed from a plurality of linked nucleotide units. The nucleotide units each include a nucleoside unit. In the context of the present invention the nucleotide units in oligonucleotides may be linked together via linkages that may be phosphorus-containing or non-phosphorus-containing. The term "oligonucleotide" also includes naturally occurring species and synthetic species formed from naturally occurring or synthetic subunits.

Oligonucleotides according to the present invention also can include modified subunits. Such modified subunits include modified portions, be they modified sugar moieties or modified base moieties, that function similarly to natural bases and natural sugars. Representative modified bases include deaza or aza purines and pyrimidines used in place of natural purine and pyrimidine bases; pyrimidines having substituent groups at the 5 or 6 position; and purines having altered or replacement substituent groups at the 2, 6, or 8 positions. Representative nucleobases include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoro-methyl and other 5-substituted uracils and cytosines, 7-methyl-guanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie*, International Edition, 1991, 30, 613–722 (see especially pages 622 and 623, and in the *Concise Encyclopedia of Polymer Science and Engineering*, J. I. Kroschwitz Ed.,. John Wiley & Sons, 1990, pages 858–859, Cook, *Anti-Cancer Drug Design* 1991, 6, 585–607, each of which are hereby incorporated by reference in their entirety). The term "nucleosidic base" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole.

Representative modified sugars include carbocyclic or acyclic sugars, sugars having substituent groups at their 2' position, sugars having substituent groups at their 3' position, and sugars having substituents in place of one or more hydrogen atoms of the sugar. Other altered base moieties and altered sugar moieties are disclosed in U.S. Pat. No. 3,687,808 and PCT application PCT/US89/02323.

Altered base moieties or altered sugar moieties also include other modifications consistent with the spirit of this invention. Such oligonucleotides are best described as being structurally distinguishable from, yet functionally interchangeable with, naturally occurring or synthetic wild type oligonucleotides. All such oligonucleotides are comprehended by this invention so long as they function effectively to mimic the structure of a desired RNA or DNA strand.

For use in antisense methodology, the oligonucleotides of the present invention preferably comprise from about 10 to about 30 subunits. It is more preferred that such oligonucleotides comprise from about 15 to about 25 subunits. As will be appreciated, a subunit is a base and a sugar combination suitably bound to adjacent subunits through a linkage such as, for example, a phosphorus-containing (e.g., phosphodiester and phosphorothioate) linkage or some other non-phosphorus-containing linking moiety. The nucleoside subunits need not be linked in any particular manner, so long as they are covalently bound. Exemplary linkages are those between the 3' and 5' positions of adjacent nucleosides, as is observed in natural nucleic acids; such linkages are referred to as "3',5'-linkages." Linkages between the 2' and 5' positions of adjacent nucleosides are refereed to as "2',5'-linkages".

It is preferred that the RNA or DNA portion which is to be modulated using oligonucleotides of the present invention be preselected to comprise that portion of DNA or RNA which codes for the protein whose formation or activity is to be modulated. The targeting portion of the composition to be employed is thus selected to be complementary to the preselected portion of the targeted DNA or RNA, that is, to be an antisense oligonucleotide for that portion.

The present invention provides oligonucleotides comprising a plurality of linked nucleotides wherein at least one of the internucleotide linkages is a 2',5'-linkage. A 2',5'-linkage is one that covalently connects the 2'-position of the sugar portion of one nucleotide subunit with the 5'-position of the sugar portion of an adjacent nucleotide subunit.

The actual linking moiety that accomplishes the 2',5'-linkage may be one of any of the many linking moieties known in the art and described in the articles and patents listed above.

The present invention further provides oligonucleotides comprising a plurality of nucleotides linked together by internucleotide linkages, wherein the linkage is selected from a group consisting of, but not limited to, phosphorus-containing and non-phosphorus-containing linkages. Phosphorus-containing linkages include, but are not limited to, phosphodiester, phosphorothioate, phosphoramidate, alkylphosphonate, N3'->P5' phosphoramidate, phosphinate, phosphate, thiophosphate and phosphorodithioate linkages. Non-phosphorus-containing linkages include, but are not limited to, glycol, ether, all carbon atom, urea, carbamate, amide, cyclic, amine, hydroxylamine, hydrazino, -substituted amide 3, and methylene(methylimino) linkages. In general, most phosphorus-containing linkages, such as the phosphorothioate, phosphoramidates, phosphonates and phosphorodithioates all result in oligonucleotides with reduced binding to complementary targets and decreased hybrid stability. In order to make effective therapeutics therefore this binding and hybrid stability of antisense oligonucleotides needs to be improved.

In a preferred embodiment, the internucleotide linkages present in the oligonucleotides of the present invention are either all phosphodiester (PO) or all phosphorothioate (PS). In a further preferred embodiment, the internucleotide linkages present in the oligonucleotides of the present invention are any combination of at least one phosphodiester and at least one phosphorothioate linkage. Oligonucleotides that bear only PO linkages are found to not only bind well to target nucleic acids but to also exhibit nuclease resistance imparted by the presence of the one or more 2',5'-linkages. Oligonucleotides that bear only PS linkages have enhanced nuclease resistance but poorer binding (due to decreased $T_m$ values for PS linkages) to their target nucleic acids. Mixed phosphorothioate/phosphodiester linked oligonucleotides are advantageous because the offer improved binding because of the presence of PO linkages, while retaining nuclease resistance imparted by the PS and 2',5'-linkages.

The present invention further provides oligonucleotides having at least one 2',5' internucleotide linkage wherein at least one of the nucleotides comprising such a linkage bears a 3'-substituent of the formula

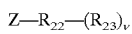

$$Z-R_{22}-(R_{23})_v$$

where:

Z is O, S, NH, or N—$R_{22}$—$(R_{23})_v$, $R_{22}$ is $C_1$–$C_{20}$ alkyl, $C_2$–$C_{20}$ alkenyl, or $C_2$–$C_{20}$ alkynyl;

$R_{23}$ is $R_{24}$ when Z is O;

otherwise $R_{23}$ is hydrogen or $R_{24}$ when Z is S, NH, or N—$R_{22}$—$(R_{23})_v$;

$R_{24}$ is amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, hydroxyalkyamino, hydroxydialkylamino, isocyanato, sulfoxide, sulfone, sulfide, disulfide, silyl, aryl, heterocycle, carbocycle, intercalator, reporter molecule, conjugate, poly-amine, polyamide, polyalkylene glycol, polyether, a group that enhances the pharmacodynamic properties of oligonucleotides, or a group that enhances the pharmacokinetic properties of oligonucleotides;

v is from 0 to about 10.

Certain performed 3'-substituents include substituents having one of the formulas:

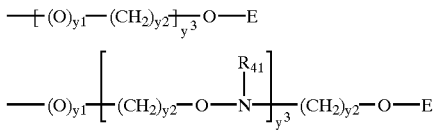

where:
y1 is 0 or 1;
y2 is 0 to 10;
y3 is 1 to 10;
E is $N(R_{41})(R_{42})$ or $N=C(R_{41})(R_{42})$; and
each $R_{41}$ and each $R_{42}$ is independently H, $C_1-C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heteroatom selected from N and O.

One particularly preferred 3'-substituents of the invention includes 3'-methoxyethoxy [3'-O—$CH_2CH_2OCH_3$, also known as 3'-O-(2-methoxyethyl) or 3'-MOE], an alkoxyalkoxy group. A further preferred modification includes 3'-dimethylaminooxyethoxy, i.e., a $O(CH_2)_2ON(CH_3)_2$ group, also known as 3'-DMAOE. The corresponding 2'-DMAOE group is described in co-owned U.S. patent application Ser. No. 09/016,520, filed on Jan. 30, 1998, the contents of which are herein incorporated by reference. Other preferred modifications include 3'-methoxy (2'-O—$CH_3$) and 3'-aminopropoxy (3'-O$CH_2CH_2CH_2NH_2$).

A preferred group of compounds of the invention include oligonucleotides having at least one 2',5' internucleotide linkage where the nucleotide of the 2' side of the 2',5' linkage includes a 3' substituent that is an alkoxyalkoxy, dialkoxyalkoxy, hydroxyalkoxy, dihydroxyalkoxy, aminoalkoxy, alkylaminoalkoxy, dialkylaminoalkoxy, dialkylaminooxyalkoxy, haloalkoxy, dihaloalkoxy or trihaloalkoxy substituent and protected versions of the same. Particularly preferred 3'-substituents include methoxyethoxy, hydroxyethoxy, dimethylaminooxyethoxy, trifluoromethylethoxy, aminopropoxy, and protected versions of the same.

This additional modification, at the 3'-position, to the structure of oligonucleotides provides enhanced properties to the oligonucleotides of the present invention. It has been observed that incorporating these unique substitutions onto the 3'-position of 2',5'-linked oligonucleotides results in enhanced binding of the oligonucleotides to their target nucleic acids. This is further reflected in generally increased $T_m$ values observed for 2'5'-linked-3'-substituted-oligonucleotides of the present invention compared to their parent oligonucleotides. Satisfactory nuclease resistance has also been demonstrated for the oligonucleotides of the present invention both in vitro and in vivo. These enhanced properties make the oligonucleotides of the present invention particularly attractive compounds for development at diagnostic and therapeutic agents.

Oligonucleotides of the invention can also include sugar substitutions, particularly O-substitutions, on the ribosyl ring. Representative substitutions for ring O include S, $CH_2$, CHF, and $CF_2$, see, e.g., Secrist, et al., *Abstract* 21, *Program & Abstracts, Tenth International Roundtable, Nucleosides, Nucleotides and their Biological Applications,* Park City, Utah, Sep. 16–20, 1992, hereby incorporated by reference in its entirety.

Additional modifications may also be made at other positions on the oligonucleotide, particularly the 3' position of the sugar on the 3' terminal nucleotide and the 5' position of 5' terminal nucleotide. For example, one additional modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553), cholic acid (Manoharan et al., *Bioorg. Med. Chem. Lett.,* 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), or adamantane acetic acid (Manoharan et al., *Tetrahedron Lett.,* 1995, 36, 3651), a palmityl moiety (Mishra et al., *Biochim. Biophys. Acta,* 1995, 1264, 229), or an octadecylamine or hexylamino-carbonyl-oxycholesterol moiety (Crooke et al., *J. Pharmacol. Exp. Ther.,* 1996, 277, 923).

As used herein, the term "alkyl" includes but is not limited to straight chain, branch chain, and cyclic unsaturated hydrocarbon groups including but not limited to methyl, ethyl, and isopropyl groups. Alkyl groups of the present invention may be substituted. Representative alkyl substituents are disclosed in U.S. Pat. No. 5,212,295, at column 12, lines 41–50, hereby incorporated by reference in its entirety.

Alkenyl groups according to the invention are to straight chain, branch chain, and cyclic hydrocarbon groups containing at least one carbon-carbon double bond, and alkynyl groups are to straight chain, branch chain, and cyclic hydrocarbon groups containing at least one carbon-carbon triply bond. Alkenyl and alkynyl groups of the present invention can be substituted.

Aryl groups are substituted and unsubstituted aromatic cyclic moieties including but not limited to phenyl, naphthyl, anthracyl, phenanthryl, pyrenyl, and xylyl groups. Alkaryl groups are those in which an aryl moiety links an alkyl moiety to a core structure, and aralkyl groups are those in which an alkyl moiety links an aryl moiety to a core structure.

In general, the term "hetero" denotes an atom other than carbon, preferably but not exclusively N, O, or S. Accordingly, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

Oligonucleotides according to the present invention that are hybridizable to a target nucleic acid preferably comprise from about 5 to about 50 nucleosides. It is more preferred that such compounds comprise from about 8 to about 30 nucleosides, with 15 to 25 nucleosides being particularly preferred. As used herein, a target nucleic acid is any nucleic acid that can hybridize with a complementary nucleic acid-like compound. Further in the context of this invention, "hybridization" shall mean hydrogen bonding, which may be Watson-Crick, Hoogsteen or reversed Hoogsteen hydrogen bonding between complementary nucleobases. "Complementary" as used herein, refers to the capacity for precise pairing between two nucleobases. For example, adenine and thymine are complementary nucleobases which pair through the formation of hydrogen bonds. "Complementary" and "specifically hybridizable," as used herein, refer to precise pairing or sequence complementarity between a first and a second nucleic acid-like oligomers containing nucleoside subunits. For example, if a nucleobase at a certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases which can hydrogen bond with each other. Thus, "specifically hybridizable" and "complementary" are terms which are used to indicate a sufficient degree of complementarity such that stable and specific binding occurs between a compound of the invention and a target RNA molecule. It is understood that an oligomeric compound of the invention need not be 100% complementary to its target RNA sequence to be specifically hybridizable. An oligomeric compound is specifically hybridizable when binding of the oligomeric compound to the target RNA molecule interferes with the normal function of the target RNA to cause a loss of utility, and there is a sufficient degree of complementarity to avoid non-specific binding of the oligomeric compound to non-target sequences under conditions in which specific binding is desired, i.e. under physiological conditions in the case of in vivo assays or therapeutic treatment, or in the case of in vitro assays, under conditions in which the assays are performed.

The present invention also provides oligonucleotides bearing methoxyethoxy substituents at one or more 2'-positions on the sugar portion of the nucleotides. When placed at the 2'-position of antisense oligonucleotides, these substituents are capable of improving the critical properties of nuclease resistance and binding. Therefore, the present invention also provides oligonucleotides that not only are 2',5'-linked-3'-substituted-oligonucleotides but are also PO, PS or mixed PO/PS in nature and may incorporate at one or more available 2'-positions appropriate substitutions. It is preferred that the 2'-substituent be a methoxyethoxy group.

The oligonucleotides of the present invention can be used in diagnostics, therapeutics and as research reagents. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes RNA-DNA transcription or RNA-protein translation as a fundamental part of its hereditary, metabolic or cellular control is susceptible to therapeutic and/or prophylactic treatment in accordance with this invention. Seemingly diverse organisms such as bacteria, yeast, protozoa, algae, all plants and all higher animal forms including warm-blooded animals, ca be treated. Further each cell of multicellular eukaryotes can be treated since they include both DNA-RNA transcription and RNA-protein translation as integral parts of their cellular activity. Many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides. As used herein, therapeutics is meant to include the eradication of a disease state, by killing an organism or by control of erratic or harmful cellular growth or expression.

Oligonucleotides according to the invention can be assembled in solution or through solid-phase reactions, for example, on a suitable DNA synthesizer utilizing nucleosides, phosphoramidites and derivatized controlled pore glass (CPG) according to the invention and/or standard nucleotide precursors. The nucleoside and nucleotide precursors used in the present invention may carry substituents either the 2' or 3' positions. Such precursors may be synthesized according to the present invention by reacting appropriately protected nucleosides bearing at least one free 2' or 3' hydroxyl group with an appropriate alkylating agent such as , but not limited to, alkoxyalkyl halides, alkoxylalkylsulfonates, hydroxyalkyl halides, hydroxyalkyl sulfonates, aminoalkyl halides, aminoalkyl sulfonates, phthalimidoalkyl halides, phthalimidoalkyl sulfonates, alkylaminoalkyl halides, alkylaminoalkyl sulfonates, dialkylaminoalkyl halides, dialkylaminoalkylsulfonates, dialkylaminooxyalkyl halides, dialkylaminooxyalkyl sulfonates and suitably protected versions of the same. Preferred halides used for alkylating reactions include chloride, bromide, fluoride and iodide. Preferred sulfonate leaving groups used for alkylating reactions include, but are not limited to, benzenesulfonate, methylsulfonate, tosylate, p-bromobenzenesulfonate, triflate, trifluoroethylsulfonate, and (2,4-dinitroanilino)benzenesulfonate.

Suitably protected nucleosides can be assembled into oligonucleotides according to known techniques. See, for example, Beaucage et al., *Tetrahedron*, 1992, 48, 2223.

The ability of oligonucleotides to bind to their complementary target strands is compared by determining the melting temperature ($T_m$) of the hybridization complex of the oligonucleotide and its complementary strand. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands. The structure-stability relationships of a large number of nucleic acid modifications have been reviewed (Freier and Altmann, *Nucl. Acids Research*, 1997, 25, 4429–443).

The relative binding ability of the oligonucleotides of the present invention was determined using protocols as described in the literature (Freier and Altmann, *Nucl. Acids Research*, 1997, 25, 4429–443). Typically absorbance versus temperature curves were determined using samples containing 4 uM oligonucleotide in 100 mM Na+, 10 mM phosphate, 0.1 mM EDTA, and 4 uM complementary, length matched RNA.

The in vivo stability of oligonucleotides is an important factor to consider in the development of oligonucleotide therapeutics. Resistance of oligonucleotides to degradation by nucleases, phosphodiesterases and other enzymes is therefore determined. Typical in vivo assessment of stability of the oligonucleotides of the present invention is performed by administering a single dose of 5 mg/kg of oligonucleotide in phosphate buffered saline to BALB/c mice. Blood collected at specific time intervals post-administration is analyzed by HPLC or capillary gel electrophoresis (CGE) to determine the amount of oligonucleotide remaining intact in circulation and the nature the of the degradation products. Increased in vivo nuclease resistance has been observed.

The CGE analysis of blood plasma samples from mice dosed with the oligonucleotides of the present invention reveals the relative nuclease resistance of 2',5'-linked oligomers compared to a uniform 2'-deoxy-phosphorothioate oligonucleotide targeted to mouse c-raf) Because of the nuclease resistance of the 2',5'-linkage, coupled with the fact that 3'-methoxyethoxy substituents are present and afford further nuclease protection the oligonucleotides of the invention were found to be more stable in plasma than the uniform 2'-deoxy-phosphorthioate oligonucleotide. Similar observations were noted in kidney and liver tissue. Thus 2',5'-linkages with 3'-substituents offer excellent nuclease resistance in plasma, kidney and liver against 5'-exonucleases and 3'-exonucleases. Thus the oligonucleotides of the present invention hold promise as antisense agents with longer durations of action.

Some oligonucleotides of the present invention have also been assessed for their activity in controlling the c-raf message in bEND cells. Comparable or better activity at controlling c-raf mRNA expression was observed with 2',5'-linked-3'-substituted oligonucleotides of the present invention.

Additional objects, advantages, and novel features of this invention will become apparent to those skilled in the art upon examination of the following examples, which are not intended to be limiting. All oligonucleotide sequences are listed in a standard 5' to 3' order from left to right.

EXAMPLE 1
5'-O-Dimethoxytrityl-2'-O-(2-methoxyethyl)-5-methyl uridine and 5'-O-Dimethoxytrityl-3'-O-(2-methoxyethyl)5-methyl uridine 2',3'-O-dibutylstannylene 5-methyl uridine was synthesized according to the procedure of Wagner et al. (*J. Org. Chem.* (1974) 39 24). 345 g of this compound was alkylated with 196 g of 2-methoxyethyl bromide in the presence of tetrabutylammonium iodide (235 g) in 3 L of DMF at 70° to give a mixture of 2'-O- and 3'-O-(2'-methoxyethyl)-5-methyl uridine of 150 g nucleoside mixture in nearly 1:1 ration of isomers. This mixture was then treated with 110 g of dimethoxytrityl chloride (DMT-Cl) in 1 liter of pyridine to give 5'-O-dimethoxytritylated nucleoside mixture. After the standard work-up, the isomers were separated in a silica gel column to separate the 2'-alkylated compound from the 3'-alkylated compound. The 2'-isomer eluted first, followed by the 3'-isomer.

EXAMPLE 2
5'-O-Dimethoxytrityl-3'-O-(2-methoxyethyl)-5-methyl-uridine-2'-O-(2-cyanoethyl-N,N-diisopropyl) phosphoramidite 5'-O-Dimethoxytrityl-3'-O-(2-methoxyethyl)-5-methyluridine (5 g, 0.008 mol) was dissolved in 30 mL of $CH_2Cl_2$ and to this solution, under argon, 0.415 g of diisopropylaminotetrazolide and 3.9 mL of 2-cyanoethoxy-N,N-diisopropyl phosphoramidite were added. The reaction was stirred overnight. The solvent was evaporated and the residue was applied to silica column and eluted with ethylacetate to give 3.75 g of the desired phosphoramidite.

EXAMPLE 3
5'-O-Dimethoxytrityl-3'-O-(2-methoxyethyl)-$N^4$-benzoyl-5-methyl-cytidine 5'-O-Dimethoxytrityl-3'-O-(2-methoxyethyl)-5-methyl uridine (15 g) was treated with 150 mL anhydrous pyridine and 4.5 mL of acetic anhydride under argon and stirred overnight. Pyridine was evaporated and the residue was partitioned between 200 mL of saturated $NaHCO_3$ solution and 200 mL of ethylacetate. The organic layer was dried (anhydrous $MgSO_4$) and evaporated to give 16 g of 2'-acetoxy-5'-O-(dimethoxytrityl)-3'-O-(2-methoxyethyl)-5-methyl uridine.

To an ice-cold solution of triazole (19.9 g) in triethylamine (50 mL) and acetonitrile (150 mL), with mechanical stirring, 9 mL of $POCl_3$ was added dropwise. After the addition, the ice bath was removed and stirred for 30 min. The 2'-acetoxy-5'-O-(dimethoxytrityl)-3'-O-(2-methoxyethyl)-5-methyl uridine (16 g in 50 mL $CH_3CN$) was added dropwise to the above solution keeping the solution again in ice bath. After 2 hrs, TLC indicated a faster moving nucleoside, C-4-triazole-derivative. The reaction flask was evaporated and the nucleoside was partitioned between ethylacetate (500 mL) and $NaHCO_3$ (500 mL). The organic layer was washed with saturated NaCl solution, dried (anhydrous $NgSO_4$) and evaporated to give 15 g of C-4-triazole nucleoside. This compound was then dissolved in 2:1 mixture of $NH_4OH$/dioxane (100 mL:200 mL) and stirred overnight. TLC indicated disappearance of the starting material. The solution was evaporated and dissolved in methanol to crystallize out 9.6 g of 5'-O-(dimethoxytrityl)-3'-O-(2-methoxyethyl)5-methyl cytidine.

5'-O-dimethoxytrityl-3'-O-(2-methoxyethyl)-5-methyl cytidine (9.6 g, 0.015 mol) was dissolved in 50 mL of DMF and treated with 7.37 g of benzoic anhydride. After 24 hrs of stirring, DMF was evaporated and the residue was loaded on silica column and eluted with 1:1 hexane:ethylacetate to give the desired nucleoside.

EXAMPLE 4
5'-O-dimethoxy-3'-O-(2-methoxyethyl)-$N^4$-benzoyl-5-methyl-cytidine-2'-O-(2-cyanoethyl-N,N-diisopropyl) phosphoramidite 5'-O-dimethoxy-3'-O-(2-methoxyethyl)-$N^4$-benzoyl-5-methyl-cytidine-2'-O-(2-cyanoethyl-N,N-diisopropyl) phosphoramidite was obtained from the above nucleoside using the phosphitylation protocol described for the corresponding 5-methyl-uridine derivative.

EXAMPLE 5
$N^6$-Benzoyl-5'-O-(4,4'-dimethoxytrityl)-3'-O-(2-methoxyethyl)adenosine A solution of adenosine (42.74 g, 0.16 mol) in dry dimethyl formamide (800 mL) at 5° C. was treated with sodium hydride (8.24 g, 60% in oil prewashed thrice with hexanes, 0.21 mol). After stirring for 30 min, 2-methoxyethyl bromide (0.16 mol) was added over 20 min. The reaction was stirred at 5° C. for 8 h, then filtered through Celite. The filtrate was concentrated under reduced pressure followed by coevaporation with toluene (2×100 mL). The residue was adsorbed on silica gel (100 g) and chromatographed (800 g, chloroform-methanol 9:1→4:1). Selected fractions were concentrated under reduced pressure and the residue was a mixture of 2'-O-(2-(methoxyethyl)adenosine and 3'-O-(2-methoxyethyl)adenosine in the ratio of 4:1.

The above mixture (0.056 mol) in pyridine (100 mL) was evaporated under reduced pressure to dryness. The residue was redissolved in pyridine (560 mL) and cooled in an ice water bath. Trimethylsilyl chloride (36.4 mL, 0.291 mol) was added and the reaction was stirred at 5° C. for 30 min. Benzoyl chloride (33.6 mL, 0.291 mol) was added and the reaction was allowed to warm to 25° C. for 2 h and then cooled to 5° C. The reaction was diluted with cold water (112 mL) and after stirring for 15 min, concentrated ammonium hydroxide (112 mL). After 30 min, the reaction was concentrated under reduced pressure (below 30° C.) followed by coevaporation with toluene (2×100 mL). The residue was dissolved in ethyl acetate-methanol (400 mL, 9:1) and the undesired silyl by-products were removed by filtration. The filtrate was concentrated under reduced pressure and then-chromatographed on silica gel (800 g, chloroform-methanol 9:1). Selected fractions were combined, concentrated under reduced pressure and dried at 25° C./0.2 mmHg for 2 h to give pure $N^6$-Benzoyl-2'-O-(2-methoxyethyl)adenosine and pure $N^6$-Benzoyl-3'-O-(2-methoxyethyl) adenosine.

A solution of $N^6$-Benzoyl-3'-O-(2-methoxyethyl) adenosine (11.0 g, 0.285 mol) in pyridine (100 mL) was evaporated under reduced pressure to an oil. The residue was redissolved in dry pyridine (300 mL) and 4,4'-dimethoxytrityl chloride (DMT-Cl, 10.9 g, 95%, 0.31 mol) was added. The mixture was stirred at 25° C. for 16 h and then poured onto a solution of sodium bicarbonate (20 g) in ice water (500 mL). The product was extracted with ethyl acetate (2×150 mL). The organic layer was washed with brine (50 mL), dried over sodium sulfate (powdered) and evaporated under reduced pressure (below 40° C.). The residue was chromatographed on silica gel (400 g, ethyl acetate-acetonitrile-triethylamine 99:1:1→95:5:1). Selected fractions were combined, concentrated under reduced pressure and dried at 25° C./0.2 mmHg to give 16.8 g (73%) of foam; TLC homogenous.

EXAMPLE 6

[$N^6$-Benzoyl-5'-O-(4,4'-dimethoxytrityl)-3'-O-(2-methoxyethyl) adenosin-2'-O-yl]-N,N-diisopropylamino-cyanoethoxyphosphoramidite The product was prepared in the same manner as the 5-methyl-cytidine and 5-methyluridine analogs of Examples 2 and 4 by starting with intermediate of Example 5 and using ethyl acetate-hexanes-triethylamine 59:40:1 as the chromatography eluent to give the product as a solid foam in 67% yield. TLC homogenous. $^{31}$P-NMR (CDCl$_3$, H$_3$PO$_4$ std.) δ147.89; 148.36 (diastereomers).

EXAMPLE 7

5'-O-(4,4'-dimethoxytrityl)-$N^2$-isobutyryl-3'-O-(2-methoxyethyl)guanosine

A. 2,6-Diaminopurine riboside

To a 2 L stainless steel Parr bomb was added guanosine hydrate (100 g, 0.35 mol, Aldrich), hexamethyl) disilazane (320 mL, 1.52 mol, 4.4 eq.), trimethyl) silyl trifluoromethanesulfonate (8.2 mL), and toluene (350 mL). The bomb was sealed and partially submerged in an oil bath (170° C.; internal T 150° C., 150 psi) for 5 days. The bomb was cooled in a dry ice/acetone bath and opened. The contents were transferred with methanol (300 mL, Note 3) to a flask and the solvent was evaporated under reduced pressure. Aqueous methanol (50%, 1.2 L) was added. The resulting brown suspension was heated to reflux for 5 h. The suspension was concentrated under reduced pressure to one half volume in order to remove most of the methanol. Water (600 mL) was added and the solution was heated to reflux, treated with charcoal (5 g) and hot filtered through Celite. The solution was allowed to cool to 25° C. The resulting precipitate was collected, washed with water (200 mL) and dried at 90° C./0.2 mmHg for 5 h to give a constant weight of 87.4 g (89%) of tan, crystalline solid; mp 247° C. (shrinks), 255° C. (dec, lit. (1) mp 250–252° C.); TLC homogenous (Rf 0.50, isopropanol-ammonium hydroxide-water 16:3:1); PMR (DMSO), δ5.73 (d, 2, 2-NH$_2$), 5.78 (s, 1, H-1), 6.83 (br s, 2, 6NH$_2$).

B. 2'-O-(2-methoxyethyl)-2,6-diaminopurine riboside and 3'-O-(2-methoxyethyl)-2,6-diaminopurine riboside To a solution of 2,6-diaminopurine riboside (1, 10.0 g, 0.035 mol) in dry dimethyl formamide (350 mL) at 0° C. under an argon atmosphere was added sodium hydride (60% in oil, 1.6 g, 0.04 mol). After 30 min., 2-methoxyethyl bromide (0.44 mol) was added in one portion and the reaction was stirred at 25° C. for 16 h. Methanol (10 mL) was added and the mixture was concentrated under reduced pressure to an oil (20 g). The crude product, containing a ratio of 4:1 of the 2'/3' isomers, was chromatographed on silica gel (500 g, chloroform-methanol 4:1). The appropriate fractions were combined and concentrated under reduced pressure to a semi-solid (12 g). This was triturated with methanol (50 mL) to give a white, hygroscopic solid. The solid was dried at 40° C./0.2 mmHg for 6 h to give a pure 2' product and the pure 3' isomer, which were confirmed by NMR.

C. 3'-O-2-(methoxyethyl)guanosine

With rapid stirring, 3'-O-(2-methoxyethyl)-2,6-diaminopurine riboside (0.078 mol) was dissolved in monobasic sodium phosphate buffer (0.1 M, 525 mL, pH 7.3–7.4) at 25° C. Adenosine deaminase (Sigma type II, 1 unit/mg, 350 mg) was added and the reaction was stirred at 25° C. for 60 h. The mixture was cooled to 5° C. and filtered. The solid was washed with water (2×25 mL) and dried at 60° C./0.2 mmHg for 5 h to give 10.7 g of first crop material. A second crop was obtained by concentrating the mother liquors under reduced pressure to 125 mL, cooling to 5° C., collecting the solid, washing with cold water (2×20 mL) and drying as above to give 6.7 g of additional material for a total of 15.4 g (31% from guanosine hydrate) of light tan solid; TLC purity 97%.

D. $N^2$-Isobutyryl-3'-O-2-(methoxyethyl)guanosine

To a solution of 3'-O-2-(methoxyethyl)guanosine (18.1 g, 0.0613 mol) in pyridine (300 mL) was added trimethyl silyl chloride (50.4 mL, 0.46 mol). The reaction was stirred at 25° C. for 16 h. Isobutyryl chloride (33.2 mL, 0.316 mol) was added and the reaction was stirred for 4 h at 25° C. The reaction was diluted with water (25 mL). After stirring for 30 min, ammonium hydroxide (concentrated, 45 mL) was added until pH 6 was reached. The mixture was stirred in a water bath for 30 min and then evaporated under reduced pressure to an oil. The oil was suspended in a mixture of ethyl acetate (600 mL) and water (100 mL) until a solution formed. The solution was allowed to stand for 17 h at 25° C. The resulting precipitate was collected, washed with ethyl acetate (2×50 mL) and dried at 60° C./0.2 mmHg for 5 h to give 16.1 g (85%) of tan solid; TLC purity 98%.

E. 5'-O-(4,4'-dimethoxytrityl)-$N^2$-isobutyryl-3'-O-(2-methoxyethyl)guanosine

A solution of $N^2$-Isobutyryl-3'-O-2-(methoxyethyl) guanosine (0.051 mol) in pyridine (150 mL) was evaporated under reduced pressure to dryness. The residue was redissolved in pyridine (300 mL) and cooled to 10–15° C. 4,4'-dimethoxytrityl chloride (DMT-Cl, 27.2 g, 95%, 0.080 mol) was added and the reaction was stirred at 25° C. for 16 h. The reaction was evaporated under reduced pressure to an oil, dissolved in a minimum of methylene chloride and applied on a silica gel column (500 g). The product was eluted with a gradient of methylene chloride-triethylamine (99:1) to methylene chloride-methanol-triethylamine (99:1:1). Selected fractions were combined, concentrated under reduced pressure and dried at 40° C./0.2 mmHg for 2 h to afford 15 g (15.5% from guanosine hydrate) of tan foam; TLC purity 98%.

EXAMPLE 8
[5'-O-(4,4'-dimethoxytrityl)-N$^2$-isobutyryl-3'-O-(2-methoxyethyl)guanosin-2'-O-yl]-N,N-diisopropylaminocyanoethoxyphosphoramidite The protected nucleoside from Example 7 (0.0486 mol) was placed in a dry 1 L round bottom flask containing a Teflon stir-bar. The flask was purged with argon. Anhydrous methylene chloride (400 mL) was cannulated into the flask to dissolve the nucleoside. Previously vacuum dried N,N-diisopropylaminohydrotetrazolide (3.0 g, 0.0174 mol) was added under argon. With stirring, bis-N,N-diisopropyl-aminocyanoethylphosphoramidite (18.8 g, 0.0689 mol) was added via syringe over 1 min (no exotherm noted). The reaction was stirred under argon at 25° C. for 16 h. After verifying the completion of the reaction by TLC, the reaction was transferred to a separatory funnel (1 L). The reaction flask was rinsed with methylene chloride (2×50 mL). The combined organic layer was washed with saturated aq. sodium bicarbonate (200 mL) and then brine (200 mL). The organic layer was dried over sodium sulfate (50 g, powdered) for 2 h. The solution was filtered and concentrated under reduced pressure to a viscous oil. The resulting phosphoramidite was purified by silica gel flash chromatography (800 g, ethyl acetate-triethylamine 99:1). Selected fractions were combined, concentrated under reduced pressure, and dried at 25° C./0.2 mmHg for 16 h to give 18.0 g (46%, 3% from guanosine hydrate) of solid foam TLC homogenous. $^{31}$P-NMR (CDCl$_3$, H$_3$PO$_4$ std.) δ_147.96; 148.20 (diastereomers).

EXAMPLE 9
5'-O-Dimethoxytrityl-3'-O-Methoxyethyl-5-Methyl-Uridine-2'-O-Succinate 5'-O-dimethoxytrityl-3'-O-(2-methoxy)ethyl-thymidine was first succinylated on the 2'-position. 4 mmols of the thymidine nucleoside were reacted with 10.2 ml dichloroethane, 615 mg (6.14 mmols) succinic anhydride, 570 μL (4.09 mmols) triethylamine, and 251 mg (2.05 mmols) 4-dimethylaminopyridine. The reactants were vortexed until dissolved and placed in heating block at 55 C. for approximately 30 minutes. Completeness of reaction checked by thin layer chromatography (TLC). The reaction mixture was washed three times with cold 10% citric acid followed by three washes with water. Organic phase removed and dried under sodium sulfate. Succinylated nucleoside was dried under P$_2$O$_5$ overnight in vacuum oven.

EXAMPLE 10
5'-O-Dimethoxytrityl-3'-O-Methoxyethyl-5-Methyl-Uridine-2'-O-Succinoyl Linked LCA CPG 5'-O-dimethoxytrityl-3'-O-(2-methoxyethyl)-2'-O-succinyl-thymidine was coupled to controlled pore glass (CPG). 1.09 g (1.52 mmol) of the succinate were dried overnight in a vacuum oven along with 4-dimethylaminopyridine (DMAP), 2,2'-dithiobis (5-nitropyridine) (dTNP), triphenylphosphine (TPP), and pre-acid washed CPG (controlled pore glass). The following day, DMAP (1.52 mmol, 186 mg) and acetonitrile (13.7 mL) were added to the succinate. The mixture was "mixed" by a magnetic stirrer under argon. In a separate flask, dTNP (1.52 mmol, 472 mg) was dissolved in acetonitrile (9.6 mL) and dichloromethane (4.1 mL) under argon. This reaction mixture was then added to the succinate. In another separate flask, TPP (1.52 mmol, 399 mg) was dissolved in acetonitrile (37 mL) under argon. This mixture was then added to the succinate/DMAP/dTNP reaction mixture. Finally, 12.23 g pre-acid washed LCA CPG (loading=115.2 μmol/g) were added to the main reaction mixture, vortexed shortly and placed on shaker for approx. 3 hours. Removed from shaker after 3 hours and the loading was checked. A small sample of CPG was washed with copious amounts of acetonitrile, dichloromethane, and then with ether. The initial loading was found to be 63 μmol/g. (3.9 mg of CPG were cleaved with trichloroacetic acid. The absorption of released trityl cation was read at 503 nm on a spectrophotometer to determine the loading.) The whole CPG sample was then washed as described above and dried under P$_2$O$_5$ overnight in vacuum oven. The following day, the CPG was capped with 25 mL CAP A (tetrahydrofuran/acetic anhydride) and 25 mL CAP B (tetrahydrofuran/pyridine/1-methyl imidazole) for approx. 3 hours on shaker. Filtered and washed with dichloromethane and ether. CPG dried under P$_2$O$_5$ overnight in vacuum oven. After drying, 12.25 g of CPG was isolated with a final loading of 90 μmol/g.

EXAMPLE 11
3'-O-Methoxyethyl-5-Methyl-N-Benzoyl-Cytidine-2'-O-Succinate

5'-O-dimethoxytrityl-3'-O-(2-methoxy)ethyl-N-benzoyl-cytidine was first succinylated on the 2'-position. 4 mmols of the cytidine nucleoside were reacted with 10.2 ml dichloroethane, 615 mg (6.14 mmols) succinic anhydride, 570 μL (4.09 mmols) triethylamine, and 251 mg (2.05 mmols) 4-dimethylaminopyridine. The reactants were vortexed until dissolved and placed in heating block at 55 C. for approximately 30 minutes. Completeness of reaction checked by thin layer chromatography (TLC). The reaction mixture was washed three times with cold 10% citric acid followed by three washes with water. Organic phase removed and dried under sodium sulfate. Succinylated nucleoside was dried under P$_2$O$_5$ overnight in vacuum oven.

EXAMPLE 12
5'-O-Dimethoxytrityl-3'-O-Methoxyethyl-5-Methyl-N-Benzoyl-Cytidine-2'-O-Succinoyl Linked LCA CPG 5'-O-dimethoxytrityl-3'-O-(2-methoxyethyl)-2'-O-succinyl-N$^4$-benzoyl cytidine was coupled to controlled pore glass (CPG). 1.05 g (1.30 mmol) of the succinate were dried overnight in a vacuum oven along with 4-dimethylaminopyridine (DMAP), 2,2'-dithiobis (5-nitropyridine) (dTNP), triphenylphosphine (TPP), and pre-acid washed CPG (controlled pore glass). The following day, DMAP (1.30 mmol, 159 mg) and acetonitrile (11.7 mL) were added to the succinate. The mixture was "mixed" by a magnetic stirrer under argon. In a separate flask, dTNP (1.30 mmol, 400 mg) was dissolved in acetonitrile (8.2 mL) and dichloromethane (3.5 mL) under argon. This reaction mixture was then added to the succinate. In another separate flask, TPP (1.30 mmol, 338 mg) was dissolved in acetonitrile (11.7 mL) under argon. This mixture was then added to the succinate/DMAP/dTNP reaction mixture. Finally, 10.46 g pre-acid washed LCA CPG (loading=115.2 μmol/g) were added to the main reaction mixture, vortexed shortly and placed on shaker for approx. 2 hours. Removed from shaker after 2 hours and the loading was checked. A small sample of CPG was washed with copious amounts of acetonitrile, dichloromethane, and then with ether. The initial loading was found to be 46 μmol/g. (3.4 mg of CPG were cleaved with trichloroacetic acid. The absorption of released trityl cation was read at 503 nm on a spectrophotometer to determine the loading.) The whole CPG sample was then washed as described above and dried under $P_2O_5$ overnight in vacuum oven. The following day, the CPG was capped with 25 mL CAP A (tetrahydrofuran/acetic anhydride) and 25 mL CAP B (tetrahydrofuran/pyridine/1-methyl imidazole) for approx. 3 hours on shaker. Filtered and washed with dichloromethane and ether. CPG dried under $P_2O_5$ overnight in vacuum oven. After drying, 10.77 g of CPG was isolated with a final loading of 63 μmol/g.

EXAMPLE 13
5'-O-Dimethoxytrityl-3'-O-Methoxyethyl-N6-Benzoyl-Adenosine-2'-O-Succinate 5'-O-dimethoxytrityl-3'-O-(2-methoxyethyl)-$N^6$-benzoyl adenosine was first succinylated on the 2'-position. 3.0 g (4.09 mmols) of the adenosine nucleoside were reacted with 10.2 ml dichloroethane, 615 mg (6.14 mmols) succinic anhydride, 570 μL (4.09 mmols) triethylamine, and 251 mg (2.05 mmols) 4-dimethylaminopyridine. The reactants were vortexed until dissolved and placed in heating block at 55 C. for approximately 30 minutes. Completeness of reaction checked by thin layer chromatography (TLC). The reaction mixture was washed three times with cold 10% citric acid followed by three washes with water. Organic phase removed and dried under sodium sulfate. Succinylated nucleoside was dried under $P_2O_5$ overnight in vacuum oven.

EXAMPLE 14
5'-O-Dimethoxytrityl-3'-O-Methoxyethyl-N6-Benzoyl-Adenosine-2'-O-Succinoyl Linked LCA CPG Following succinylation, 5'-O-dimethoxytrityl-3'-O-(2-methoxyethyl)-2'-O-succinyl-$N^6$-benzoyl adenosine was coupled to controlled pore glass (CPG). 3.41 g (4.10 mmol) of the succinate were dried overnight in a vacuum oven along with 4-dimethylaminopyridine (DMAP), 2,2'-dithiobis (5-nitro-pyridine) (dTNP), triphenylphosphine (TPP), and pre-acid washed CPG (controlled pore glass). The following day, DMAP (4.10 mmol, 501 mg) and acetonitrile (37 mL) were added to the succinate. The mixture was "mixed" by a magnetic stirrer under argon. In a separate flask, dTNP (4.10 mmol, 1.27g) was dissolved in acetonitrile (26 mL) and dichloromethane (11 mL) under argon. This reaction mixture was then added to the succinate. In another separate flask, TPP (4.10 mmol, 1.08 g) was dissolved in acetonitrile (37 mL) under argon. This mixture was then added to the succinate/DMAP/dTNP reaction mixture. Finally, 33 g pre-acid washed LCA CPG (loading=115.2 μmol/g) were added to the main reaction mixture, vortexed shortly and placed on shaker for approx. 20 hours. Removed from shaker after 20 hours and the loading was checked. A small sample of CPG was washed with copious amounts of acetonitrile, dichloromethane, and then with ether. The initial loading was found to be 49 μmol/g. (2.9 mg of CPG were cleaved with trichloroacetic acid. The absorption of released trityl cation was read at 503 nm on a spectrophotometer to determine the loading.) The whole CPG sample was then washed as described above and dried under $P_2O_5$ overnight in vacuum oven. The following day, the CPG was capped with 50 mL CAP A (tetrahydrofuran/acetic anhydride) and 50 mL CAP B (tetrahydrofuran/pyridine/1-methyl imidazole) for approx. 1 hour on shaker. Filtered and washed with dichloromethane and ether. CPG dried under $P_2O_5$ overnight in vacuum oven. After drying, 33.00 g of CPG was obtained with a final loading of 66 μmol/g.

EXAMPLE 15
5'-O-Dimethoxytrityl-3'-O-Methoxyethyl-N2-Isobutyryl-Guanosine-2'-O-Succinate 5'-O-dimethoxytrityl-3'-O-(2-methoxyethy)l-$N^2$-isobutyryl guanosine was succinylated on the 2'-sugar position. 3.0 g (4.20 mmols) of the guanosine nucleoside were reacted with 10.5 ml dichloroethane, 631 mg (6.30 mmols) succinic anhydride, 585 μL (4.20 mmols) triethylamine, and 257 mg (2.10 mmols) 4-dimethylaminopyridine. The reactants were vortexed until dissolved and placed in heating block at 55 C. for approximately 30 minutes. Completeness of reaction checked by thin layer chromatography (TLC). The reaction mixture was washed three times with cold 10% citric acid followed by three washes with water. Organic phase removed and dried under sodium sulfate. Succinylated nucleoside was dried under $P_2O_5$ overnight in vacuum oven.

EXAMPLE 16
5'-O-Dimethoxytrityl-3'-O-Methoxyethyl-N2-Isobutyryl-Guanosine-2'-O-Succinoyl Linked LCA CPG Following succinylation, 5'-O-dimethoxytrityl-3'-O-(2-methoxyethyl)-2'-O-succinyl-$N^2$-benzoyl guanosine was coupled to controlled pore glass (CPG). 3.42 g (4.20 mmol) of the succinate were dried overnight in a vacuum oven along with 4-dimethylaminopyridine (DMAP), 2,2'-dithiobis (5-nitro-pyridine) (dTNP), triphenylphosphine (TPP), and pre-acid washed CPG (controlled pore glass). The following day, DMAP (4.20 mmol, 513 mg) and acetonitrile (37.5 mL) were added to the succinate. The mixture was "mixed" by a magnetic stirrer under argon. In a separate flask, dTNP (4.20 mmol, 1.43 g) was dissolved in acetonitrile (26 mL) and dichloromethane (11 mL) under argon. This reaction mixture was then added to the succinate. In another separate flask, TPP (4.20 mmol, 1.10 g) was dissolved in acetonitrile (37. 5 mL) under argon. This mixture was then added to the succinate/DMAP/dTNP reaction mixture. Finally, 33.75 g pre-acid washed LCA CPG (loading=115.2 μmol/g) were added to the main reaction mixture, vortexed shortly and placed on shaker for approx. 20 hours. Removed from shaker after 20 hours and the loading was checked. A small sample of CPG was washed with copious amounts of acetonitrile, dichloromethane, and then with ether. The initial loading was found to be 64 μmol/g. (3.4 mg of CPG were cleaved with trichloroacetic acid. The absorption of released trityl cation was read at 503 nm on a spectrophotometer to determine the loading.) The whole CPG sample was then washed as described above and dried under $P_2O_5$ overnight in vacuum oven. The following day, the CPG was capped with 50 mL CAP A (tetrahydrofuran/acetic anhydride) and 50 mL CAP B (tetrahydrofuran/pyridine/1-methyl imidazole) for approx. 1 hour on shaker. Filtered and washed with dichloromethane and ether. CPG dried under $P_2O_5$ overnight in vacuum oven. After drying, 33.75 g. of CPG was isolated with a final loading of 72 μmol/g.

EXAMPLE 17
5'-O-Dimethoxytrityl-3'-O-[Hexyl-(w-phthalimido)]-Uridine

2',3'-O-Dibutyl stannylene-uridine was synthesized according to the procedure of Wagner et. al., *J. Org. Chem.*, 1974, 39, 24. This compound was dried over $P_2O_5$ under vacuum for 12 hours. To a solution of this compound (29 g, 42.1 mmols) in 200 ml of anhydrous DMF were added (16.8 g, 55 mmols) of 6-bromohexyl phthalimide and 4.5 g of sodium iodide and the mixture was heated at 130° C. for 16 hours under argon. The reaction mixture was evaporated, co-evaporated once with toluene and the gummy tar residue was applied on a silica column (500 g). The column was washed with 2 L of ethyl acetate (EtOAc) followed by eluting with 10% methanol (MeOH):90% EtOAc. The product, 2'- and 3'-isomers of O-hexyl-Ω-N-phthalimido uridine, eluted as an inseparable mixture ($R_f$=0.64 in 10% MeOH in EtOAc). By $^{13}$C NMR, the isomeric ration was about 55% of the 2' isomer and about 45% of the 3' isomer. The combined yield was 9.2 g (46.2%). This mixture was dried under vacuum and re-evaporated twice with pyridine. It was dissolved in 150 mL anhydrous pyridine and treated with 7.5 g of dimethyocytrityl chloride (22.13 mmols) and 500 mg of dimethylaminopyridine (DMAP). After 2 hour, thin layer chromatography (TLC; 6:4 EtOAc:Hexane) indicated complete disappearance of the starting material and a good separation between 2' and 3' isomers ($R_f$=0.29 for the 2' isomer and 0.12 for the 3' isomer). The reaction mixture was quenched by the addition of 5 mL of $CH_3OH$ and evaporated under reduced pressure. The residue was dissolved in 300 mL $CH_2Cl_2$, washed successively with saturated $NaHCO_3$ followed by saturated NaCl solution. It was dried over $Mg_2SO_4$ and evaporated to give 15 g of a brown foam which was purified on a silica gel (500 g) to give 6.5 g of the 2'-isomer and 3.5 g of the 3' isomer.

EXAMPLE 18
5'-O-Dimethoxytrityl-3'-O-[Hexyl-(w-phthalimido)]-Uridine-2'-O-(2-cyanoethyl-N,N,-diisopropyl) Phosphoramidite 5'-dimethoxytrityl-3'-O-[hexyl-(omega-N-phthalimido)-amino]uridine (2 g, 2.6 mmol) was dissolved in 20 mL anhydrous $CH_2Cl_2$. To this solution diisopropylaminotetrazolide (0.2 g, 1.16 mmol) and 2.0 mL 2-cyanoethyl-N,N,N', N'-tetraisopropyl phosphoramidite (6.3 mmol) were added and stirred overnight. TLC (1:1 EtOAc/hexane) showed complete disappearance of starting material. The reaction mixture was transferred with $CH_2Cl_2$ and washed with saturated $NaHCO_3$ (100 mL), followed by saturated NaCl solution. The organic layer was dried over anhydrous $Na_2SO_4$ and evaporated to yield 3.8 g of a crude product, which was purified in a silica column (200 g) using 1:1 hexane/EtOAc to give 1.9 g (1.95 mmol, 74% yield) of the desired phosphoramidite.

EXAMPLE 19
Preparation of 5'-O-Dimethoxytrityl-3'-O-[Hexyl-(w-phthalimido)]-Uridine-2'-O-Succinoyl-aminopropyl CPG Succinylated and capped aminopropyl controlled pore glass (CPG; 500 Å pore diameter, aminopropyl CPG, 1.0 grams prepared according to Damha et. al., *Nucl. Acids Res.* 1990, 18, 3813.) was added to 12 ml anhydrous pyridine in a 100 ml round-bottom flask. 1-(3-Dimethylaminopropyl)-3-ethyl-carbodiimide (DEC; 0.38 grams, 2.0 mmol)], triethylamine (TEA; 100 μl, distilled over $CaH_2$), dimethylaminopyridine (DMAP; 0.012 grams, 0.1 mmol) and nucleoside 5'-O-dimethoxytrityl-3'-O-[hexyl-(Ω-N-phthalimidoamino)]uridine (0.6 grams, 0.77 mmol) were added under argon and the mixture shaken mechanically for 2 hours. More nucleoside (0.20 grams) was added and the mixture shaken an additional 24 hours. CPG was filtered off and washed successively with dichloromethane, triethylamine, and dichloromethane. The CPG was then dried under vacuum, suspended in 10 ml piperidine and shaken 15 minutes. The CPG was filtered off, washed thoroughly with dichloromethane and again dried under vacuum. The extent of loading (determined by spectrophotometric assay of dimethoxytrityl cation in 0.3 M p-toluenesulfonic acid at 498 nm) was approximately 28 μmol/g. The 5'-O-(dimethoxytrityl)-3'-O-[hexyl-(Ω-N-phthal-imidoamino]uridine-2'-O-succinyl-aminopropyl controlled pore glass was used to synthesize the oligomers in an ABI 380B DNA synthesizer using phosphoramidite chemistry standard conditions. A four base oligomer 5'-GACU*-3' was used to confirm the structure of 3'-O-hexylamine tether introduced into the oligonucleotide by NMR. As expected a multiplet signal was observed between 1.0–1.8 ppm in $^1$H NMR.

EXAMPLE 20
5'-O-Dimethoxytrityl-3'-O-[Hexylamino]-Uridine

5'-O-(dimethoxytrityl)-3'-O-[hexyl-(Ω-N-phthalimido amino)]uridine (4.5 grams, 5.8 mmol) is dissolved in 200 ml methanol in a 500 ml flask. Hydrazine (1 ml, 31 mmol) is added to the stirring reaction mixture. The mixture is heated to 60–65° in an oil bath and refluxed 14 hours. Solvent is evaporated in vacuo. The residue is dissolved in dichloromethane (250 ml) and extracted twice with an equal volume $NH_4OH$. The organic layer is evaporated to yield the crude product which NMR indicates is not completely pure. $R_f$=0 in 100% ethyl acetate. The product is used in subsequent reactions without further purification.

EXAMPLE 21
3'-O-[Propyl-(w-phthalimido)]-Adenosine

To a solution of adenosine (20.0 g, 75 mmol) in dry dimethylformamide (550 ml) at 5° C. was added sodium hydride (60% oil, 4.5 g, 112 mmol). After one hour, N-(3-bromopropyl)-phthalimide (23.6 g, 86 mmol) was added and the temperature was raised to 30° C. and held for 16 hours. Ice is added and the solution evaporated in vacuo to a gum. The gum was partitioned between water and ethyl acetate (4×300 ml). The organic phase was separated, dried, and evaporated in vacuo and the resultant gum chromatographed on silica gel (95/5 $CH_2Cl_2$/MeOH) to give a white solid (5.7 g) of the 2'-O-(propylphthalimide)adenosine. Those fractions containing the 3'-O-(propylphthalimide)adenosine were rechromatographed on silica gel using the same solvent system.

Crystallization of the 2'-O-(propylphthalimide)adenosine fractions from methanol gave a crystalline solid, m.p. 123–124° C. $^1$H NMR (400 MHZ: DMSO-$d_6$) δ1.70 (m, 2H, $CH_2$), 3.4–3.7 (m, 6H, $C_5'$, $CH_2$, $OCH_2$, Phth $CH_2$), 3.95 (q, 1H, $C_4'H$), 4.30 (q, 1H, $C_5'H$), 4.46 (t, 1H, $C_2'H$), 5.15 (d, 1H, $C_3'OH$), 5.41 (t, 1H, $C_5'OH$), 5.95 (d, 1H, $C_1'H$) 7.35 (s, 2H, $NH_2$), 7.8 (brs, 4H, Ar), 8.08 (s, 1H, $C_2H$) and 8.37 (s, 1H, $C_8H$). Anal. Calcd. $C_{21}H_{22}N_6O_6$: C, 55.03; H, 4.88; N, 18.49. Found: C, 55.38; H, 4.85; N, 18.46.

Crystallization of the 3'-(propylphthalimide)adenosine fractions from $H_2O$ afforded an analytical sample, m.p. 178–179° C. $^1$H NMR (400 MHZ: DMSO-$d_6$) δ5.86 (d, 1H, H-1'),

EXAMPLE 22
3'-O-[Propyl-(w-phthalimido)]-N6-Benzoyl-Adenosine

3'-O-(Propylphthalimide)adenosine is treated with benzoyl chloride in a manner similar to the procedure of Gaffney, et al., *Tetrahedron Lett.* 1982, 23, 2257. Chromatography on silica gel (ethyl acetate-methanol) gives the title compound.

EXAMPLE 23
3'-O-[Propyl-(w-phthalimido)]-5'-O-Dimethoxytrityl-N6-Benzoyl-Adenosine To a solution of 3'-O-(propylphthalimide)-$N^6$-benzoyl-adenosine (4.0 g) in pyridine (250 ml) is added 4,4'-dimethoxy-trityl chloride (3.3 g). The reaction is stirred for 16 hours. The reaction is added to ice/water/ethyl acetate, the organic layer separated, dried, and concentrated in vacuo and the resultant gum chromatographed on silica gel (ethyl acetate-methanol triethylamine) to give the title compound.

EXAMPLE 24
3'-O-[Propyl-(w-phthalimido)]-5'-O-Dimethoxytrityl-N6-Benzoyl-Adenosine-2'-O-(N,N-diisopropyl-b-cyanoethyl)Phosphoramidite 3'-O-(Propylphthalimide)-5'-O-dimethoxytrityl-$N^6$-benzoyladenosine is treated with (β-cyanoethoxy)chloro-N,N-diisopropyl)aminophosphane in a manner similar to the procedure of Seela, et al., *Biochemistry* 1987, 26, 2233. Chromatography on silica gel (EtOAc/hexane) gives the title compound as a white foam.

EXAMPLE 25
3'-O-(Aminopropyl)-Adenosine

A solution of 3'-O-(propylphthalimide)adenosine (8.8 g, 19 mmol), 95% ethanol (400 ml) and hydrazine (10 ml, 32 mmol) is stirred for 16 hrs at room temperature. The reaction mixture is filtered and filtrate concentrated in vacuo. Water (150 ml) is added and acidified with acetic acid to pH 5.0. The aqueous solution is extracted with EtOAc (2×30 ml) and the aqueous phase is concentrated in vacuo to afford the titled compound as a HOAc salt.

EXAMPLE 26
3'-O-[3-(N-trifluoroacetamido)propyl]-Adenosine

A solution of 3'-O-(propylamino)adenosine in methanol (50 ml) and triethylamine (15 ml, 108 mmol) is treated with ethyl trifluoroacetate (18 ml, 151 mmol). The reaction is stirred for 16 hrs and then concentrated in vacuo and the resultant gum chromatographed on silica gel (9/1, EtOAc/MeOH) to give the title compound.

EXAMPLE 27
N6-Dibenzoyl-3'-O-[3-(N-trifluoroacetamido)propyl]-Adenosine

3'-O-[3-(N-trifluoroacetamido)propyl]adenosine is treated as per Example 22 using a Jones modification wherein tetrabutylammonium fluoride is utilized in place of ammonia hydroxide in the work up. The crude product is purified using silica gel chromatography (EtOAc→EtOAc/MeOH 1/1) to give the title compound.

EXAMPLE 28
N6-Dibenzoyl-5'-O-Dimethoxytrityl-3'-O-[3-(N-trifluoroacetamido)propyl]-Adenosine 4,4'-Dimethoxytrityl chloride (3.6 g, 10.0 mmol.) Is added to a solution of $N^6$-(dibenzoyl)-3'-O-[3-(N-trifluoroacetamido)propyl)adenosine in pyridine (100 ml) at room temperature and stirred for 16 hrs. The solution is concentrated in vacuo and chromatographed on silica gel (EtOAc/TEA 99/1) to give the title compound.

EXAMPLE 29
N6-Dibenzoyl-5'-O-Dimethoxytrityl-3'-O-[3-(N-trifluoroacetamido)propyl]-Adenosine-2'-O-(N,N,-diisopropyl-b-cyanoethyl)Phosphoramidite A solution of $N^6$-(dibenzoyl)-5'-O-(dimethoxytrityl)-3'-O-[3-(N-trifluoroacetamido)propyl]adenosine in dry $CH_2Cl_2$ is treated with bis-N,N-diisopropylamino cyanoethyl phosphite (1.1 eqiv) and N,N-diisopropylaminotetrazolide (catalytic amount) at room temperature for 16 hrs. The reaction is concentrated in vacuo and chromatographed on silica gel (EtOAc/hexane/TEA 6/4/1) to give the title compound.

EXAMPLE 30
3'-O-(Butylphthalimido)-Adenosine

The title compound is prepared as per Example 21, using N-(4-bromobutyl)phthalimide in place of the 1-bromopropane. Chromatography on silica gel (EtOAC-MeOH) gives the title compound. $^1$H NMR (200 MHZ, DMSO-$d_6$) δ5.88 (d, 1H, $C_1$H).

EXAMPLE 31
N6-Benzoyl-3'-O-(Butylphthalimido)-Adenosine

Benzoylation of 3'-O-(butylphthalimide)adenosine as per Example 22 gives the title compound.

EXAMPLE 32
N6-Benzoyl-5'-O-Dimethoxytrityl-3'-O-(Butyl-phthalimido)-Adenosine The title compound is prepared from 3'-O-(butyl-phthalimide)-$N^6$-benzoyladenosine as per Example 22.

EXAMPLE 33
N6-Benzoyl-5'-O-Dimethoxytrityl-3'-O-(Butyl-phthalimido)-Adenosine-2'-O-(N,N,-diisopropyl-b-cyanoethyl)Phosphoramidite The title compound is prepared from 3'-O-(butylphthal-imide)-5'-O-dimethoxytrityl-$N^6$-benzoyladenosine as per Example 24.

EXAMPLE 34
3'-O-(Pentylphthalimido)-Adenosine

The title compound is prepared as per Example 21, using N-(5-bromopentyl)phthalimide. The crude material from the extraction is chromatographed on silica gel using $CHCl_3$/MeOH (95/5) to give a mixture of the 2' and 3' isomers. The 2' isomer is recrystallized from EtOH/MeOH 8/2. The mother liquor is rechromatographed on silica gel to afford the 3' isomer.

2'-O-(Pentylphthalimido)adenosine: M.P. 159–160° C. Anal. Calcd. for $C_{23}H_{24}N_6O_5$: C, 57.26; H, 5.43; N, 17.42. Found: C, 57.03; H, 5.46; N, 17.33.

3'-O-(Pentylphthalimido)adenosine: $^1$H NMR (DMSO-$d_6$) δ5.87 (d, 1H, H-1').

EXAMPLE 35
N6-Benzoyl-3'-O-(Butylphthalimido)-Adenosine

Benzoylation of 3'-O-(pentylphthalimide)adenosine is achieved as per the procedure of Example 22 to give the title compound.

EXAMPLE 36
N6-Benzoyl-5'-O-Dimethoxytrityl-3'-O-(Butyl-phthalimido)-Adenosine The title compound is prepared from 3'-O-(pentyl-phthalimide)-$N^6$-benzoyladenosine as per the procedure of Example 23. Chromatography on silica gel (ethylacetate, hexane, triethylamine), gives the title compound.

EXAMPLE 37
N6-Benzoyl-5'-O-Dimethoxytrityl-3'-O-(Butyl-phthalimido)-Adenosine-2'-O-(N,N,-diisopropyl-b-cyanoethyl)Phosphoramidite The title compound is prepared from 3'-O-(pentyl-phthalimide)-5'-O-(dimethoxytrityl)-$N^6$-benzoyladenosine as per the procedure of Example 24 to give the title compound.

EXAMPLE 38

3'-O-(Propylphthalimido)-uridine

A solution of uridine-tin complex (48.2 g, 115 mmol) in dry DMF (150 ml) and N-(3-bromopropyl)phthalimide (46 g, 172 mmol) was heated at 130° C. for 6 hrs. The crude product was chromatographed directly on silica gel $CHCl_3$/MeOH 95/5. The isomer ration of the purified mixture was 2'/3' 81/19. The 2' isomer was recovered by crystallization from MeOH. The filtrate was rechromatographed on silica gel using $CHCl_3 \rightarrow CHCl_3$/MeOH (95/5) gave the 3' isomer as a foam.

2'-O-(Propylphthalimide)uridine: Analytical sample recrystallized from MeOH, m.p. 165.5–166.5° C., $^1$H NMR (200 MHZ, DMSO-$d_6$) $\delta$1.87 (m, 2H, $CH_2$), 3.49–3.65 (m, 4H, $C_2$H), 3.80–3.90 (m, 2H, $C_3H_1C_4H$), 4.09 (m, 1H, $C_2H$), 5.07 (d, 1h, $C_3OH$), 5.16 (m, 1H, $C_5OH$), 5.64 (d, 1H, CH=), 7.84 (d, 1H, $C_1H$), 7.92 (bs, 4H, Ar), 7.95 (d, 1H, CH=) and 11.33 (s, 1H, ArNH). Anal. $C_{20}H_{21}N_3H_8$, Calcd, C, 55.69; H, 4.91; N, 9.74. Found, C, 55.75; H, 5.12; N, 10.01.

3'-O-(Propylphthalimide)uridine: $^1$H NMR (DMSO-$d_6$) $\delta$5.74 (d, 1H, H-1').

EXAMPLE 39

3'-O-(Aminopropyl)-Uridine

The title compound is prepared as per the procedure of Example 25.

EXAMPLE 40

3'-O-[3-(N-trifluoroacetamido)propyl]-Uridine

3'-O-(Propylamino)uridine is treated as per the procedure of Example 26 to give the title compound.

EXAMPLE 41

5'-O-Dimethoxytrityl-3'-O-[3-(N-trifluoroacetamido)propyl]-Uridine

3'-O-[3-(N-trifluoroacetamido)propyl]uridine is treated as per the procedure of Example 28 to give the title compound.

EXAMPLE 42

5'-O-Dimethoxytrityl-3'-O-[3-(N-trifluoroacetamido)propyl]-Uridine-2'-O-(N,N,-diisopropyl-b-cyanoethyl)Phosphoramidite 5'-O-(Dimethoxytrityl)-3'-O-[3-(N-trifluoroacetamido)-propyl]uridine is treated as per the procedure of Example 29 to give the title compound.

EXAMPLE 43

3'-O-(Propylphthalimido)-Cytidine

The title compounds were prepared as per the procedure of Example 21.

2'-O-(propylphthalimide)cytidine: $^1$H NMR (200 MHZ, DMSO-$d_6$) $\delta$5.82 (d, 1H, $C_1H$).

3'-O-(propylphthalimide)cytidine: $^1$H NMR (200 MHZ, DMSO-$d_6$) $\delta$5.72 (d, 1H, $C_1H$).

EXAMPLE 44

3'-O-(Aminopropyl)-Cytidine

3'-O-(Propylphthalimide)cytidine is treated as per the procedure of Example 25 to give the title compound.

EXAMPLE 45

3'-O-[3-(N-trifluoroacetamido)propyl]-Cytidine

3'-O-(Propylamino)cytidine is treated as per the procedure of Example 26 to give the title compound.

EXAMPLE 46

N4-Benzoyl-3'-O-[3-(N-trifluoroacetamido)propyl]-Cytidine

3'-O-[3-(N-trifluoroacetamido)propyl]cytidine is treated as per the procedure of Example 27 to give the title compound.

EXAMPLE 47

N4-Benzoyl-5'-O-Dimethoxytrityl-3'-O-[3-(N-trifluoroacetamido)propyl]-Cytidine $N^4$-(Benzoyl)-3'-O-[3-(N-trifluoroacetamido)propyl]-cytidine is treated as per the procedure of Example 28 to give the title compound.

EXAMPLE 48

N4-Benzoyl-5'-O-Dimethoxytrityl-3'-O-[3-(N-trifluoroacetamido)propyl]-Cytidine-2'-O-(N,N,-diisopropyl-b-cyanoethyl)Phosphoramidite $N^4$-(Benzoyl)-5'-O-(dimethoxytrityl)-3'-O-[3-(N-trifluoroacetamido)propyl]cytidine is treated as per the procedure of Example 29 to give the title compound.

EXAMPLE 49

Oligonucleotide Synthesis

Oligonucleotides were synthesized on a Perseptive Biosystems Expedite 8901 Nucleic Acid Synthesis System. Multiple 1-$\mu$mol syntheses were performed for each oligonucleotide. Trityl groups were removed with trichloroacetic acid (975 $\mu$L over one minute) followed by an acetonitrile wash. All standard amidites (0.1M) were coupled twice per cycle (total coupling time was approximately 4 minutes). All novel amidites were dissolved in dry acetonitrile (100 mg of amidite/1 mL acetonitrile) to give approximately 0.08–0.1 M solutions. Total coupling time was approximately 6 minutes (105 $\mu$L of amidite delivered). 1-H-tetrazole in acetonitrile was used as the activating agent. Excess amidite was washed away with acetonitrile. (1S)-(+)-(10-camphorsulfonyl)oxaziridine (CSO, 1.0 g CSO/8.72 ml dry acetonitrile) was used to oxidize (4 minute wait step) phosphodiester linkages while 3H-1,2-benzodithiole-3-one-1,1-dioxide (Beaucage reagent, 3.4 g Beaucage reagent/200 mL acetonitrile) was used to oxidize (one minute wait step) phosorothioate linkages. Unreacted functionalities were capped with a 50:50 mixture of tetrahyrdofuran/acetic anhydride and tetrahydrofuran/pyridine/1-methyl imidazole. Trityl yields were followed by the trityl monitor during the duration of the synthesis. The final DMT group was left intact. The oligonucleotides were deprotected in 1 mL 28.0–30% ammonium hydroxide ($NH_4OH$) for approximately 16 hours at 55 C.

Oligonucleotides were also made on a larger scale (20 $\mu$mol/synthesis). Trityl groups were removed with just over 8 mL of trichloroacetic acid. All standard amidites (0.1 M) were coupled twice per cycle (13 minute coupling step). All novel amidites were also coupled four times per cycle but the coupling time was increased to approximately 20 minutes (delivering 480 $\mu$L of amidite). Oxidation times remained the same but the delivery of oxidizing agent increased to approximately 1.88 mL per cycle. Oligonucleotides were cleaved and deprotected in 5 mL 28 0–30% $NH_4OH$ at 55 C., for approximately 16 hours.

TABLE I

3'-O-(2-methoxyethyl) containing 2'-5' linked oligonucleotides

| ISIS # | Sequence (5'-3')[1] | Backbone | Chemistry | SEQ ID No. |
|---|---|---|---|---|
| 17176 | ATG—CAT—TCT—GCC—CCC—AAG—GA* | P = S | 3'-O—MOE | 1 |
| 17177 | ATG—CAT—TCT—GCC—CCC—AAG—G*A* | P = S | 3'-O—MOE | 1 |
| 17178 | ATG—CAT—TCT—GCC—CCC—AAG$_o$—G*$_o$A* | P = S/P = O | 3'-O—MOE | 1 |
| 17179 | A*TG—CAT—TCT—GCC—CCC—AAG—GA* | P = S | 3'-O—MOE | 1 |
| 17180 | A*TG—CAT—TCT—GCC—CCC—AAG—G*A* | P = S | 3'-O—MOE | 1 |
| 17181 | A*$_o$TG—CAT—TCT—GCC—AAA—AAG$_o$—G*$_o$A* | P = S/P = O | 3'-O—MOE | 1 |
| 21415 | A*T*G—CAT—TCT—GCC—AAA—AAG—G*A* | P = S | 3'-O—MOE | 1 |
| 21416 | A*$_o$T*$_o$G—CAT—TCT—GCC—AAA—AAG$_o$—G*$_o$A* | P = S/P = O | 3'-O—MOE | 1 |
| 21945 | A*A*A* | P = O | 3'-O—MOE | 2 |
| 21663 | A*A*A*A* | P = O | 3'-O—MOE | 3 |
| 20389 | A*U*C*G* | P = O | 3'-O—MOE | 4 |
| 20390 | C*G*C*—G*A*A*—T*T*C*—G*C*G* | P = O | 3'-O—MOE | 5 |

[1]All nucleosides with an asterisk contain 3'-O-(2-methoxyethyl).

EXAMPLE 50
Oligonucleotide Purification

After the cleavage and deprotection step, the crude oligonucleotides synthesized in Example 49 were filtered from CPG using Gelman 0.45 μm nylon acrodisc syringe filters. Excess NH$_4$OH was evaporated away in a Savant AS160 automatic speed vac. The crude yield was measured on a Hewlett Packard 8452A Diode Array Spectrophotometer at 260 nm. Crude samples were then analyzed by mass spectrometry (MS) on a Hewlett Packard electrospray mass spectrometer and by capillary gel electrophoresis (CGE) on a Beckmann P/ACE system 5000. Trityl-on oligonucleotides were purified by reverse phase preparative high performance liquid chromatography (HPLC).

HPLC conditions were as follows: Waters 600E with 991 detector; Waters Delta Pak C4 column (7.8×300 mm); Solvent A: 50 mM triethylammonium acetate (TEA-Ac), pH 7.0; B: 100% acetonitrile; 2.5 mL/min flow rate; Gradient: 5% B for first five minutes with linear increase in B to 60% during the next 55 minutes. Larger oligo yields from the larger 20 μmol syntheses were purified on larger HPLC columns (Waters Bondapak HC18HA) and the flow rate was increased to 5.0 mL/min. Appropriate fractions were collected and solvent was dried down in speed vac. Oligonucleotides were detritylated in 80% acetic acid for approximately 45 minutes and lyophilized again. Free trityl and excess salt were removed by passing detritylated oligonucleotides through Sephadex G-25 (size exclusion chromatography) and collecting appropriate samples through a Pharmacia fraction collector. Solvent again evaporated away in speed vac. Purified oligonucleotides were then analyzed for purity by CGE, HPLC (flow rate: 1.5 mL/min; Waters Delta Pak C4 column, 3.9×300 mm), and MS. The final yield was determined by spectrophotometer at 260 nm.

TABLE II

Physical characteristics of 3'-O-(2-methoxyethyl) containing 2'-5' linked oligonucleotides.

|  | Expected Mass | Observed Mass | HPLC[2] T$_R$ (min.) | # Ods (260 nm) Purified |
|---|---|---|---|---|
| 17176 | 6440.743 | 6440.300 | 23.47 | 3006 |
| 17177 | 6514.814 | 6513.910 | 23.67 | 3330 |
| 17178 | 6482.814 | 6480.900 | 23.06 | 390 |
| 17179 | 6513.798 | 6513.560 | 23.20 | 3240 |
| 17180 | 6588.879 | 6588.200 | 23.96 | 3222 |
| 17181 | 6540.879 | 6539.930 | 23.01 |  |
| 21415 | 6662.976 | 6662.700 | 24.18 | 4008 |
| 21416 | 6598.969 | 6597.800 | 23.01 | 3060 |
| 21945 | 1099.924 | 1099.300 | 19.92 | 121 |
| 21663 | 1487.324 | 1486.800 | 20.16 | 71 |
| 20389 | 1483.000 | 1482.000 |  | 62 |
| 20390 | 4588.000 | 4591.000 |  | 151 |

[2]Conditions: Waters 600E with detector 991; Waters C4 column (3.9 × 300 mm); Solvent A: 50 mM TEA—Ac, pH 7.0; B: 100% acetonitrile; 1.5 mL/min. flow rate; Gradient: 5% B for first five minutes with linear increase in B to 60% during the next 55 minutes.

EXAMPLE 51
T$_m$ Studies on Modified Oligonucleotides

Oligonucleotides synthesized in Examples 49 and 50 were evaluated for their relative ability to bind to their complementary nucleic acids by measurement of their melting temperature (T$_m$). The melting temperature (T$_m$), a characteristic physical property of double helices, denotes the temperature (in degrees centigrade) at which 50% helical (hybridized) versus coil (unhybridized) forms are present. T$_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher T$_m$. The higher the T$_m$, the greater the strength of the bonds between the strands.

The test oligonucleotides and the complementary nucleic acid were incubated at a standard concentration of 4 μM for each oligonucleotide in buffer (100 mM NaCl, 10 mM sodium phosphate, pH 7.0, 0.1 mM EDTA). Samples were heated to 90 C. and the initial absorbance taken using a Guilford Response II Spectrophotometer (Corning). Samples were then slowly cooled to 15 C. and then the change in absorbance at 260 nm was monitored with heating during the heat denaturation procedure. The temperature was increased by 1 degree C/absorbance reading and the denaturation profile analyzed by taking the 1$^{st}$ derivative of the melting curve. Data was also analyzed using a two-state linear regression analysis to determine the Tm's. The results of these tests for the some of the oligonucleotides from Examples 49 and 50 are shown in Table III:

TABLE III

Tm Analysis of Oligonucleotides

| ISIS # | Sequence (5'-3') | Backbone | $T_m$ © | # Mods | #2'-5' Linkages | SEQ ID No. |
|---|---|---|---|---|---|---|
| 11061 | ATG—CAT—TCT—GCC—CCC—AAG—GA | P = S | 61.4 | 0 | 0 | 1 |
| 17176 | ATG—CAT—TCT—GCC—CCC—AAG—GA* | P = S | 61.4 | 1 | 0 | 1 |
| 17177 | ATG—CAT—TCT—GCC—CCC—AAG—G*A* | P = S | 61.3 | 2 | 1 | 1 |
| 17178 | ATG—CAT—TCT—GCC—CCC—AAG$_o$—G*$_o$A* | P = S/P = O | 61.8 | 2 | 1 | 1 |
| 17179 | A*TG—CAT—TCT—GCC—CCC—AAG—GA* | P = S | 61.1 | 2 | 1 | 1 |
| 17180 | A*TG—CAT—TCT—GCC—CCC—AAG—G*A* | P = S | 61.0 | 3 | 2 | 1 |
| 17181 | A*$_o$TG—CAT—TCT—GCC—AAA—AAG$_o$—G*$_o$A* | P = S/P = O | 61.8 | 3 | 2 | 1 |
| 21415 | A*T*G—CAT—TCT—GCC—AAA—AAG—G*A* | P = S | 61.4 | 4 | 3 | 1 |
| 21416 | A*$_o$T*$_o$G—CAT—TCT—GCC—AAA—AAG$_o$—G*$_o$A* | P = S/P = O | 61.7 | 4 | 3 | 1 |

[1]All nucleosides with an asterisk contain 3'-O-(2-methoxyethyl).

EXAMPLE 52
NMR Experiments on Modified Oligonucleotides Comparison of 3',5' versus 2',5' Internucleotide Linkages and 2'-Substituents versus 3'-Substituents by NMR The 400 MHz $^1$H spectrum of oligomer d(GAU$_2$*CT), where U$_2$=2'-O-aminohexyluridine showed 8 signals between 7.5 and 9.0 ppm corresponding to the 8 aromatic protons. In addition, the anomeric proton of U* appears as a doublet at 5.9 ppm with $J_{1',2'}$=7.5 Hz, indicative of C2'-endo sugar puckering. The corresponding 2'-5' linked isomer shows a similar structure with $J_{1',2'}$=3.85 Hz at 5.75 ppm, indicating an RNA type sugar puckering at the novel modification site favorable for hybridization to an mRNA target. The proton spectrum of the oligomer d(GACU$_3$*), where U$_3$*=3'-O-hexylamine, showed the expected 7 aromatic proton signals between 7.5 and 9.0 ppm and the anomeric proton doublet at 5.9 ppm with $J_{1',2'}$=4.4 Hz. This suggests more of a C3'-endo puckering for the 3'-O- alkylamino compounds compared to their 2' analogs. $^{31}$P NMR of these oligonucleotides showed the expected 4 and 3 signals from the internucleotide phosphate linkages for d(GAU*CT) and d(GACU*), respectively. 3'-5' linked vs. 2'-5' linked have different retention times in RP HPLC and hence different lipophilicities, implying potentially different extent of interactions with cell membranes.

EXAMPLE 53
$T_m$ Analysis of 2',5$^1$-Linked Oligonucleotides versus 3',5'-Linked Oligonucleotides Thermal melts were done as per standarized literature procedures. Oligonucleotide identity is as follows:

Oligonucleotide A is a normal 3'-5' linked phosphodiester oligodeoxyribonucleotide of the sequence d(GGC TGU* CTG CG) where the * indicates the attachment site of a 2'-aminolinker.

Oligonucleotide B is a normal 3'-5' linked phosphodiester oligoribonucleotide of the sequence d(GGC TGU* CTG CG) where the * indicates the attachment site of either a 2'-aminolinker. Each of the ribonucleotides of the oligonucleotide, except the one bearing the * substituent, are 2'-O-methyl ribonucleotides.

Oligonucleotide C is has 2'-5' linkage at the * position in addition to a 3'-aminolinker at this site. The remainder of the oligonucleotide is a phosphodiester oligodeoxyribonucleotide of the sequence d(GGC TGU* CTG CG). The base oligonucleotide (no 2'-aminolinker) was not included in the study.

| OLIGONUCLEOTIDE | MODIFICATION | DNA TARGET | RNA TARGET |
|---|---|---|---|
| A | none | 52.2 | 54.1 |
|  | 2'-aminolinker | 50.9 | 55.5 |
| B | none | 51.5 | 72.3 |
|  | 2'-aminolinker | 49.8 | 69.3 |
| C | none | NA |  |
|  | 3'-aminolinker | 42.7 | 51.7 |

The 2'-5' linkages demonstrated a higher melting temperature against an RNA target compared to a DNA target.

EXAMPLE 54
Snake Venom Phosphodiesterase and Liver Homogenate Experiments on Oligonucleotide Stability The following oligonucleotides were synthesized following the procedure of Example 49.

TABLE IV

Modified Oligonucleotides synthesized to evaluate stability

| ISIS # | Sequence (5'-3') | Backbone | Chemistry | SEQ ID No. |
|---|---|---|---|---|
| 22110 | TTT—TTT—TTT—TTT—TTT—T*T*T*—T* | P = O | 3'-O—MOE | 6 |
| 22111 | TTT—TTT—TTT—TTT—TTT—T#T#T#—U# | P = O | 3'-O—MOE | 7 |
| 22112 | TTT—TTT—TTT—TTT—TTT—T*T*T*—T* | P = S | 3'-O—MOE | 6 |
| 22113 | TTT—TTT—TTT—TTT—TTT—T#T#T#—U# | P = S | 3'-O—MOE | 7 |
| 22114 | TTT—TTT—TTT—TTT—TTT$_o$—T*$_o$T*$_o$T*$_o$T* | P = S/P = O | 3'-O—MOE | 6 |
| 22115 | TTT—TTT—TTT—TTT—TTT$_o$—T#$_o$T#$_o$T#$_o$—U# | P = S/P = O | 3'-O—MOE | 7 |

[1]All nucleosides with an asterisk contain 3'-O-(2-methoxyethyl). All nucleosides with a # contain 2'-O-(2-methoxyethyl).

The oligonucleotides were purified following the procedure of Example 50 and analyzed for their structure.

CSO-8 for phosphodiesters. The trityl reports indicated normal coupling results.

TABLE V

Properties of Modified Oligonucleotides

| ISIS # | Sequence (5'-3')[1] | Expected Mass | Observed Mass | HPLC[2] $T_R$ (min.) | # Ods (260 nm) Purified | SEQ ID No. |
|---|---|---|---|---|---|---|
| 22110 | TTT—TTT—TTT—TTT—TTT—T*T*T*—T* | 6314.189 | 6315.880 | 20.39 | 174 | 6 |
| 22111 | TTT—TTT—TTT—TTT—TTT—T#T#T#—U# | 6004.777 | 5997.490 | 20.89 | 147 | 7 |
| 22112 | TTT—TTT—TTT—TTT—TTT—T*T*T*—T* | 6298.799 | 6301.730 | 25.92 | 224 | 6 |
| 22113 | TTT—TTT—TTT—TTT—TTT—T#T#T#—U# | 6288.745 | 6286.940 | 24.77 | 209 | 7 |
| 22114 | TTT—TTT—TTT—TTT—TTT$_o$—T*$_o$T*$_o$T*$_o$—T* | 6234.799 | 6237.150 | 24.84 | 196 | 6 |
| 22115 | TTT—TTT—TTT—TTT—TTT$_o$—T#$_o$T#$_o$T#$_o$—U# | 6224.745 | 6223.780 | 23.30 | 340 | 7 |

[1]All nucleosides with an asterisk contain 3'-O-(2-methoxyethyl). All nucleosides with a # contain 2'-O-(2-methoxy) ethyl.
[2]Conditions: Waters 600E with detector 991; Waters C4 column (3.9 × 300 mm); Solvent A: 50 mM TEA—Ac, pH 7.0; B: 100% acetonitrile; 1.5 mL/min. flow rate; Gradient: 5% B for first five minutes with linear increase in B to 60% during the next 55 minutes.

EXAMPLE 55
3'-O-Aminopropyl Modified Oligonucleotides

The following modified 3'-amidites were used in the above sequences in addition to any conventional amidites as needed:

N6-Benzoyl-3'-O-propylphthalimido-A-2'-amidite, 2'-O-propylphthaloyl-A-3'-amidite, 2'-O-methoxyethyl-thymidine-3'-amidite (RIC, Inc.), 2'-O-MOE-G-3'-amidite (RIC), 2'-O-methoxyethyl-5-methylcytidine-3'-amidite, 2'-O-methoxyethyl-adenosine-3'-amidite (RIC), and 5-methylcytidine-3'-amidite. 3'-propylphthalimido-A and 2'-propylphthalimido-A were used as the LCA-CPG solid support.

The required amounts of the amidites were placed in dried vials, dissolved in acetonitrile (unmodified nucleosides were made into 1M solutions and modified nucleosides were 100 mg/mL), and connected to the appropriate ports on a Millipore Expedite™ Nucleic Acid Synthesis System (ISIS 4). 60 mg of solid support resin was used in each column for 2×1 μmole scale synthesis (2 columns for each oligo were used) The synthesis was run using the IBP-PS (1 μmole) coupling protocol for phosphorothioate backbones and CSO-8 for phosphodiesters. The trityl reports indicated normal coupling results.

After synthesis the oligonucleotides were deprotected with conc. ammonium hydroxide(aq) containing 10% of a solution of 40% methylamine (aq) at 55 C. for approximately 16 hrs. Then they were evaporated, using a Savant AS160 Automatic SpeedVac, (to remove ammonia) and filtered to remove the CPG-resin.

The crude samples were analyzed by MS, HPLC, and CE. Then they were purified on a Waters 600E HPLC system with a 991 detector using a Waters C4 Prep. scale column (Alice C4 Prep. 10-16-96) and the following solvents: A: 50 mM TEA-Ac, pH 7.0 and B: acetonitrile utilizing the "MPREP2" method.

After purification the oligonucleotides were evaporated to dryness and then detritylated with 80% acetic acid at room temp. for approximately 30 min. Then they were evaporated.

The oligonucleotides were then dissolved in conc. ammonium hydroxide and run through a column containing Sephadex G-25 using water as the solvent and a Pharmacia LKB SuperFrac fraction collector. The resulting purified oligonucleotides were evaporated and analyzed by MS, CE, and HPLC.

TABLE VI

Oligonucleotides bearing Aminopropyl Substituents

| ISIS # | Sequence (5'-3')[1] | Backbone | SEQ ID No. |
|---|---|---|---|
| 23185-1 | A*TG—CAT—TCT—GCC—CCC—AAG—GA* | P = S | 1 |
| 23186-1 | A*TG—CAT—TCT—GCC—CCC—AAG—GA* | P = S | 1 |
| 23187-1 | A*$_o$T$_o$G$_o$—C$_o$A$_s$T$_s$—T$_s$C$_s$T$_s$—G$_s$C$_s$C$_s$—C$_s$C$_s$C$_s$—A$_o$A$_o$G$_o$—G$_o$A* | P = S/P = O | 1 |
| 23980-1 | A*$_o$T$_o$G$_o$—C$_o$A$_s$T$_s$—T$_s$C$_s$T$_s$—G$_s$C$_s$C$_s$—C$_s$C$_s$C$_s$—A$_o$A$_o$G$_o$—G$_o$A* | P = S/P = O | 1 |
| 23981-1 | A*TG—CAT—TCT—GCC—CCC—AAG—GA* | P = S | 1 |
| 23982-1 | A*TG—CAT—TCT—GCC—CCC—AAG—GA* | P = S | 1 |

[1]All underlined nucleosides bear a 2'-O-methoxyethyl substituent; internucleotide linkages in PS/PO oligonucleotides are indicated by subscript 's' and 'o' notations respectively;.
A* = 3'-aminopropyl-A; A* = 2'-aminopropyl-A; C = 5-methyl-C

TABLE VII

Aminopropyl Modified Oligonucleotides

| ISIS # | Expected Mass (g/mol) | Observed Mass (g/mol) | HPLC Retention Time (min) | CE Retention Time (min) | Crude Yield (Ods) | Final Yield (Ods) |
|---|---|---|---|---|---|---|
| 23185-1 | 6612.065 | 6610.5 | 23.19 | 5.98 | 948 | 478 |
| 23186-1 | 7204.697 | 7203.1 | 24.99 | 6.18 | 1075 | 379 |
| 23187-1 | 7076.697 | 7072.33 | 23.36 | 7.56 | 838 | 546 |
| 23980-1 | 7076.697 | 7102.31 | 23.42 | 7.16 | 984 | 373 |
| 23981-1 | 7204.697 | 7230.14 | 25.36 | 7.18 | 1170 | 526 |
| 23982-1 | 6612.065 | 6635.71 | 23.47 | 7.31 | 1083 | 463 |

EXAMPLE 56
In vivo Stability of Modified Oligonucleotides

The in vivo stability of some of the modified oligonucleotides synthesized in Examples 49 and 55 was determined in BALB/c mice. Following a single i.v. administration of 5 mg/kg of oligonucleotide, blood samples were drawn at various time intervals and analyzed by CGE.

For each oligonucleotide tested, 9 male BALB/c mice (Charles River, Wilmington, Mass.) weighing about 25 g were used. Following a one week acclimatization the mice received a single tail-vein injection of oligonucleotide (5 mg/kg) administered in phosphate buffered saline (PBS), pH 7.0. One retro-orbital bleed (either at 0.25, 0.5, 2 or 4 h post-dose) and a terminal bleed (either 1, 3, 8, or 24 h post-dose) were collected from each group. The terminal bleed (approximately 0.6–0.8 ml) was collected by cardiac puncture following ketamine/xylazine anesthesia. The blood was transferred to an EDTA-coated collection tube and centrifuged to obtain plasma. At termination, the liver and kidneys were collected from each mouse. Plasma and tissue homogenates were used for analysis to determine intact oligonucleotide content by CGE. All samples were immediately frozen on dry ice after collection and stored at −80 C. until analysis.

The CGE analysis inidcated the relative nuclease resistance of 2',5'-linked oligomers compared to ISIS 11061 (uniformly 2'-deoxy-phosphorothioate oligonucleotide targeted to mouse c-raf). Because of the nuclease resistance of the 2',5'-linkage, coupled with the fact that 3'-methoxyethoxy substituents are present and afford further nuclease protection the oligonucleotides ISIS 17176, ISIS 17177, ISIS 17178, ISIS 17180, ISIS 17181 and ISIS 21415 were found to be more stable in plasma, while ISIS 11061 was not. Similar observations were noted in kidney and liver tissue. This implies that 2',5'-linkages with 3'-methoxyethoxy substituents offer excellent nuclease resistance in plasma, kidney and liver against 5'-exonucleases and 3'-exonucleases. Thus oligonucleotides with longer durations of action can be designed by incorporating both the 2',5'-linkage and 3'-methoxyethoxy motifs into their structure. It was also observed that 2',5'-phosphorothioate linkages are more stable than 2',5'-phosphodiester linkages.

A plot of the percentage of full length oligonucleotide remaining intact in plasma one hour following administration of an i.v. bolus of 5 mg/kg oligonucleotide is shown in FIG. 1.

Figure 2:
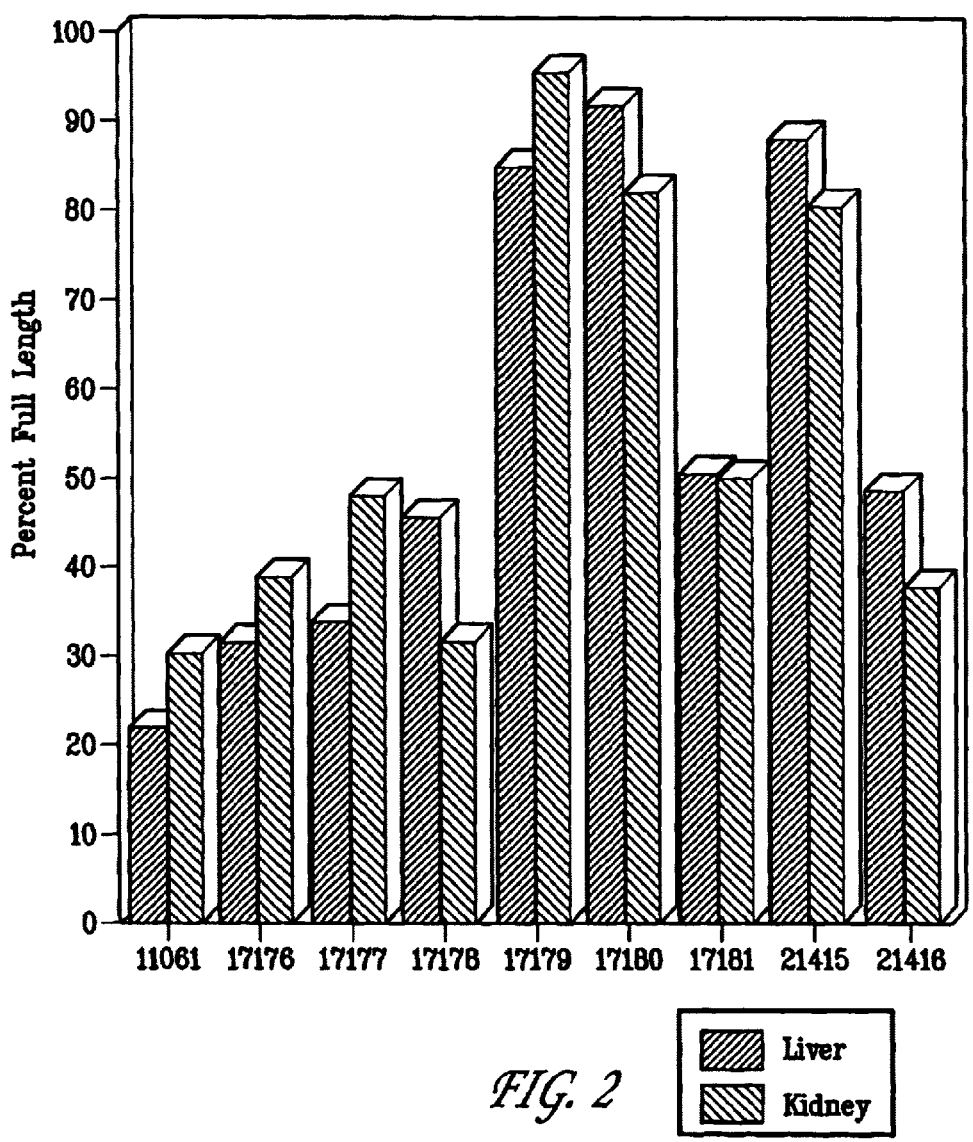
FIG. 2 shows the stability of modified oligonucleotides in mouse tissue 24 h. after i.v. bolus administration.

A plot of the percentage of full length oligonucleotide remaining intact in tissue 24 hours following administration of an i.v. bolus of 5 mg/kg oligonucleotide is shown in FIG. 2.

Figure 3:
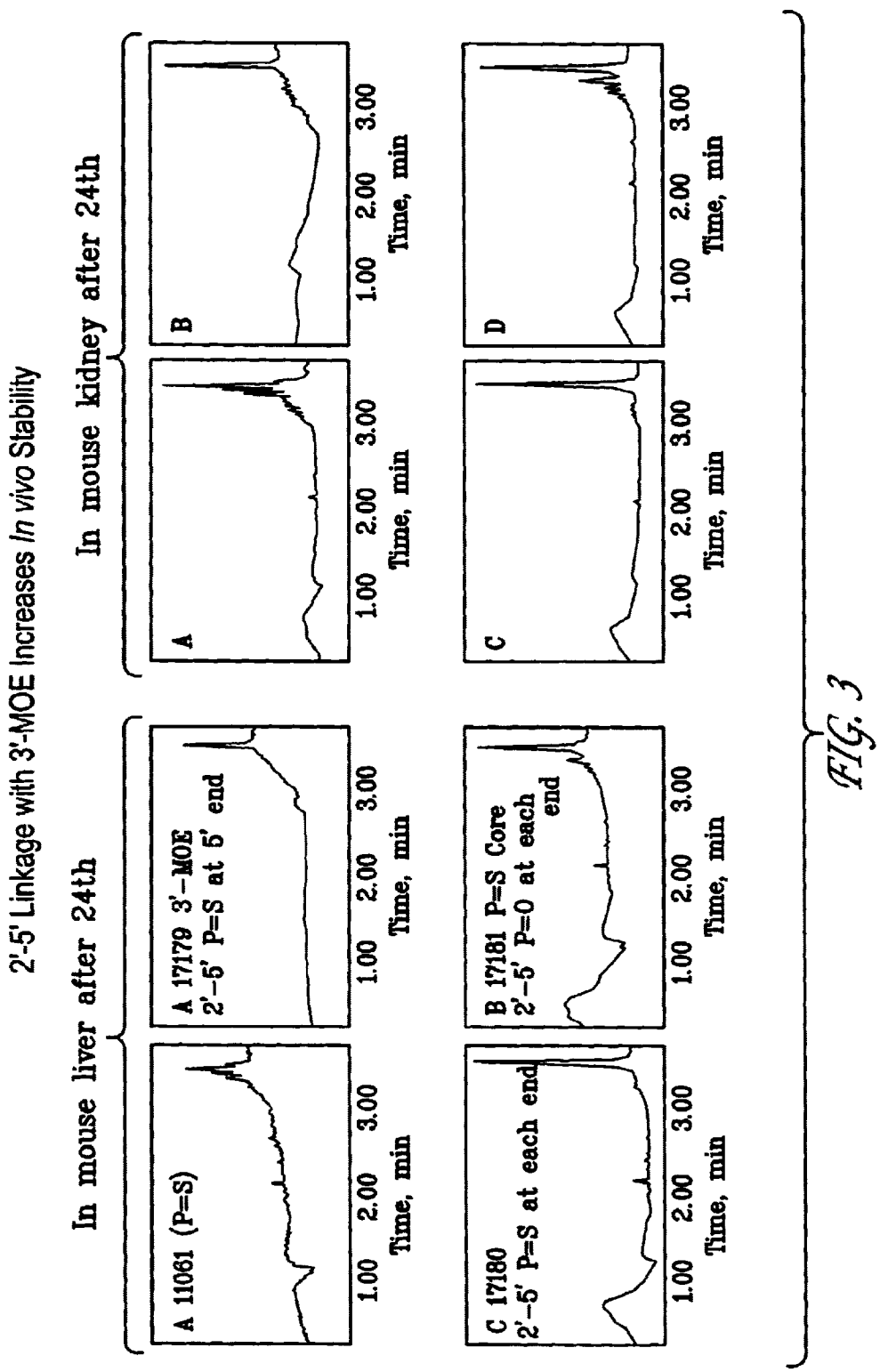
FIG. 3 shows increased in vivo stability of modified oligonucleotides of the invention as compared to a phosphorothioate oligonucleotide in tissue samples isolated from mouse liver and mouse kidney.

CGE traces of test oligonucleotides and a standard phosphorothioate oligonucleotide in both mouse liver samples and mouse kidney samples after 24 hours are shown in FIG. 3. As is evident from these traces, there is a greater amount of intact oliogonucleotide for the oligonucleotides of the invention as compared to the standard seen in panel A. The oligonucleotide shown in panel B included one substituent of the invention at each of the 5' and 3' ends of a phosphorothioate oligonucleotide while the phosphorothioate oligonucleotide seen in panel C included one substituent at the 5' end and two at the 3' end. The oligonucleotide of panel D include a substituent of the invention incorporated in a 2',5' phosphodiester linkage at both its 5' and 3' ends. While while less stable than the oligonucleotide seen in panels B and C, it is more stable than the full phosphorothioate standard oligonucleotide of panel A.

EXAMPLE 57
Control of c-raf Message in bEND Cells Using Modified Oligonucleotides In order to assess the activity of some of the oligonucleotides, an in vitro cell culture assay was used that measures the cellular levels of c-raf expression in bEND cells.

Cells and Reagents

The bEnd.3 cell line, a brain endothelioma, was the kind gift of Dr. Werner Risau (Max-Planck Institute). Opti-MEM, trypsin-EDTA and DMEM with high glucose were purchased from Gibco-BRL (Grand Island, N.Y.). Dulbecco's PBS was purchased from Irvine Scientific (Irvine, Calif.). Sterile, 12 well tissue culture plates and Facsflow solution were purchased from Becton Dickinson (Mansfield, Mass.). Ultrapure formaldehyde was purchased from Polysciences (Warrington, Pa.). NAP-5 columns were purchased from Pharmacia (Uppsala, Sweden).

Oligonucleotide Treatment

Cells were grown to approximately 75% confluency in 12 well plates with DMEM containing 4.5 g/L glucose and 10% FBS. Cells were washed 3 times with Opti-MEM prewarmed to 37° C. Oligonucleotide was premixed with a cationic lipid (Lipofectin reagent, (GIBCO/BRL) and, serially diluted to desired concentrations and transferred on to washed cells for a 4 hour incubation at 37° C. Media was then removed and replaced with normal growth media for 24 hours for northern blot analysis of mRNA.

Northern Blot Analysis

For determination of mRNA levels by Northern blot analysis, total RNA was prepared from cells by the guanidinium isothiocyanate procedure (Monia et al., *Proc. Natl. Acad. Sci. USA*, 1996, 93, 15481–15484) 24 h after initiation of oligonucleotide treatment. Total RNA was isolated by centrifugation of the cell lysates over a CsCl cushion. Northern blot analysis, RNA quantitation and normalization to G#PDH mRNA levels were done according to the reported procedure. (Dean and McKay, *Proc. Natl. Acad. Sci. USA*, 1994, 91, 11762–11766).

In bEND cells the 2',5'-linked-3'-O-methoxyethyl oligonucleotides showed reduction of c-raf message activity as a function of concentration. The fact that these modified oligonucleotides retained activity promises reduced frequency of dosing with these oligonucleotides which also show increased in vivo nuclease resistance. All 2',5'-linked oligonucleotides retained the activity of parent 11061 oligonucleotide and improved the activity even further.

Figure 4:
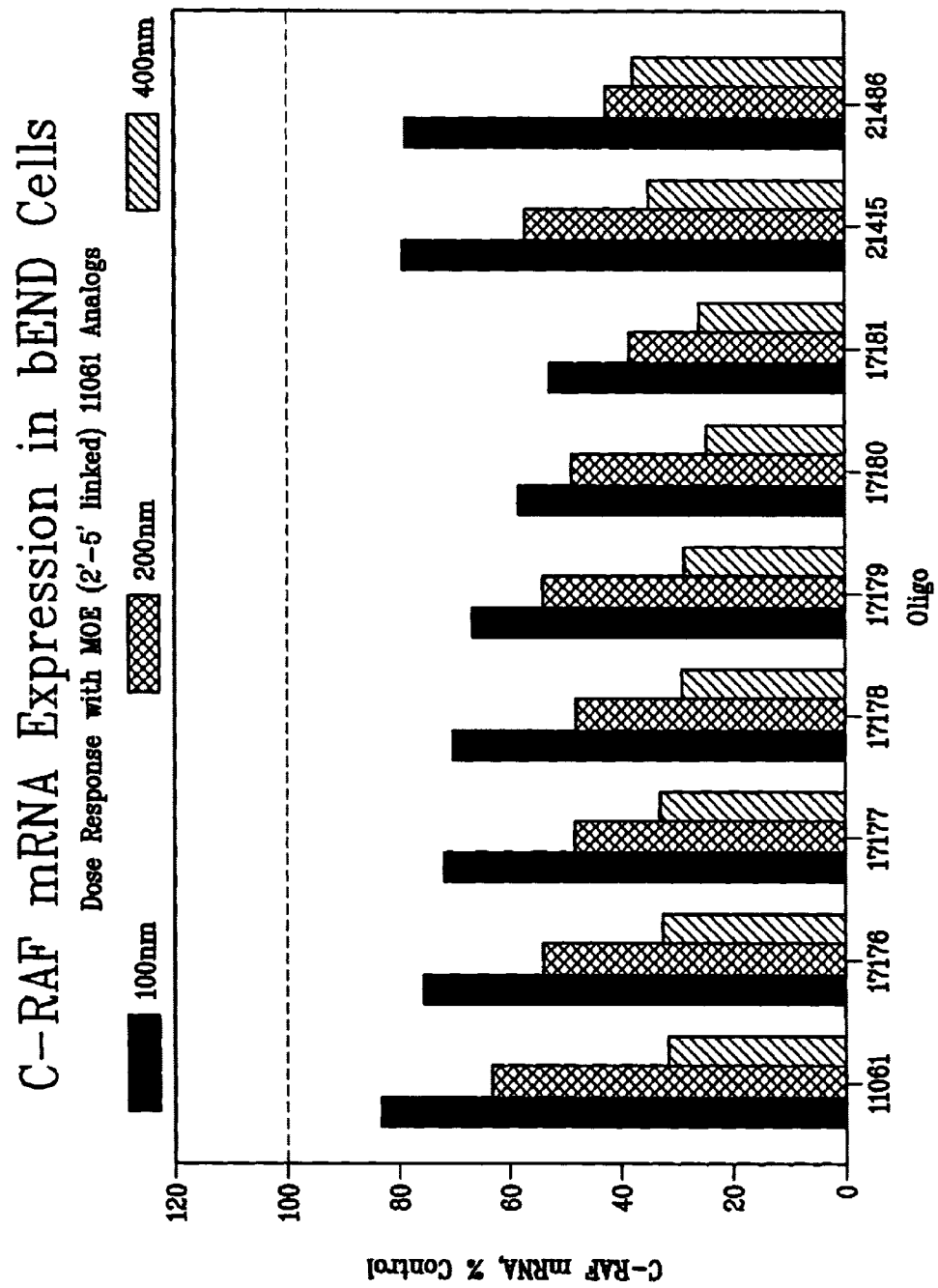
FIG. 4 shows the effects of modified oligonucleotides on c-raf mRNA expression in bEND cells.

A graph of the effect of the oligonucleotides of the present invention on c-raf expression (compared to control) in bEND cells is shown in FIG. 4.

It is intended that each of the patents, applications, printed publications and other published documents mentioned or referred to in this specification be herein incorporated by reference in their entirety.

What is claimed is:

1. An oligonucleotide comprising a plurality of nucleotides covalently linked together by internucleotide linkages, wherein at least one of said internucleotide linkages is selected from the group consisting of phosphodiester linkages and phosphorothioate linkages and at least one of said nucleotides is linked to an adjacent nucleotide by a 2',5'-internucleotide linkage and bears a 3'-substituent of the formula $$Z-R_{22}-(R_{23})_v$$

where:

Z is O, S, NH, or $N-R_{22}-(R_{23})_v$;

$R_{22}$ is $C_1-C_{20}$ alkyl, $C_2-C_{20}$ alkenyl, or $C_2-C_{20}$ alkynyl;

$R_{23}$ is $R_{24}$ when Z is O or S;

$R_{23}$ is hydrogen or $R_{24}$ when Z is NH or $N-R_{22}-(R_{23})_v$;

$R_{24}$ is amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, hydroxyalkyamino, hydroxydialkylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

v is from 0 to about 10;

provided that when Z is O or S and $R_{22}$ is $C_1-C_{20}$ alkyl or $C_2-C_{20}$ alkenyl, v is 1 to about 10.

2. The oligonucleotide of claim 1 wherein said 3'-substituent is alkoxyalkoxy, dialkoxyalkoxy, hydroxyalkoxy, dihydroxyalkoxy, aminoalkoxy, alkylaminoalkoxy, dialkylaminoalkoxy, dialkylaminooxyalkoxy, haloalkoxy, dihaloalkoxy or trihaloalkoxy.

3. The oligonucleotide of claim 1 wherein all of said internucleotide linkages are phosphorodiester linkages.

4. The oligonucleotide of claim 1 wherein all of said internucleotide linkages are phosphorothioate linkages.

5. The oligonucleotide of claim 1 wherein at least one of said internucleotide linkages is a phosphodiester linkage and at least one of said internucleotide linkages is a phosphorothioate linkage.

6. The oligonucleotide of claim 1 wherein said 3'-substituent is methoxyethoxy.

7. An oligonucleotide comprising a plurality of nucleotides covalently linked together by internucleotide linkages, wherein at least one of said nucleotides is linked to an adjacent nucleotide by a 2',5'-internucleotide linkage and bears a 3'-substituent of the formula $$Z-R_{22}-(R_{23})_v$$

where:

Z is O, S, NH, or $N-R_{22}-(R_{23})_v$ $R_{22}$ is $C_1-C_{20}$ alkyl, $C_2-C_{20}$ alkenyl, or $C_2-C_{20}$ alkynyl;

$R_{23}$ is $R_{24}$ when Z is O;

$R_{23}$ is hydrogen or $R_{24}$ when Z is S, NH, or $N-R_{22}-(R_{23})_v$;

$R_{24}$ is amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, hydroxyalkyamino, hydroxydialkylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

v is from 0 to about 10; and wherein said 3'-substituent is dimethylaminooxyethoxy.

8. The oligonucleotide of claim 1 wherein said 3'-substituent is hydroxyethoxy.

9. An oligonucleotide comprising a plurality of nucleotides covalently linked together by internucleotide linkages, wherein at least one of said nucleotides is linked to an adjacent nucleotide by a 2',5'-internucleotide linkage and bears a 3'-substituent of the formula

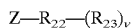

where:

Z is O, S, NH, or N—$R_{22}$—$(R_{23})_v$ $R_{22}$ is $C_1$–$C_{20}$ alkyl, $C_2$–$C_{20}$ alkenyl, or $C_2$–$C_{20}$ alkynyl;

$R_{23}$ is $R_{24}$ when Z is O;

$R_{23}$ is hydrogen or $R_{24}$ when Z is S, NH, or N—$R_{22}$—$(R_{23})_v$;

$R_{24}$ is amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, hydroxyalkyamino, hydroxydialkylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

v is from 0 to about 10; and wherein said 3'-substituent is trifluromethylethoxy.

10. An oligonucleotide comprising a plurality of nucleotides covalently linked together by internucleotide linkages, wherein at least one of said nucleotides is linked to an adjacent nucleotide by a 2',5'-internucleotide linkage and bears a 3'-substituent of the formula

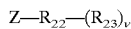

where:

Z is O, S, NH, or N—$R_{22}$—$(R_{23})_v$ $R_{22}$ is $C_1$–$C_{20}$ alkyl, $C_2$–$C_{20}$ alkenyl, or $C_2$–$C_{20}$ alkynyl;

$R_{23}$ is $R_{24}$ when Z is O;

$R_{23}$ is hydrogen or $R_{24}$ when Z is S, NH, or N—$R_{22}$—$(R_{23})_v$;

$R_{24}$ is amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, hydroxyalkyamino, hydroxydialkylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

v is from 0 to about 10; and wherein said 3'-substituent is aminopropoxy.

11. The oligonucleotide of claim 1 wherein Z is O.

12. The oligonucleotide of claim 11 wherein:

$R_{22}$ is $C_1$–$C_{20}$ alkyl; and $R_{24}$ is O-alkyl, S-alkyl, NH-alkyl, N-dialkyl, hydroxylamino, hydroxyalkyamino or hydroxydialkylamino.

13. An oligonucleotide comprising a plurality of nucleotides covalently linked together by internucleotide linkages, wherein at least one of said nucleotides is linked to an adjacent nucleotide by a 2',5'-internucleotide linkage and bears a 3'-substituent having one of the formulas:

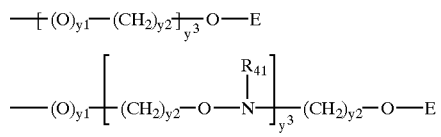

where:

y1 is 0 or 1;

y2 is 0 to 10;

y3 is 1 to 10;

E is $N(R_{41})(R_{42})$ or $N=C(R_{41})(R_{42})$; and each $R_{41}$ and each $R_{42}$ is independently H, $C_1$–$C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heteroatom selected from N and O.

14. An oligonucleotide of claim 13 wherein y3 is 1.

15. An oligonucleotide of claim 13 wherein y3 is 1.

16. An oligonucleotide of claim 13 wherein y2 is 2.

* * * * *

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
atgcattctg cccccaagga                                              20

<210> SEQ ID NO 2
<211> LENGTH: 3
<212> TYPE: DNA
<213> ORGANISM: Artificial Sequence
<220> FEATURE:
<223> OTHER INFORMATION: Synthetic construct

<400> SEQUENCE: 2 aaa                                                                 3

<210> SEQ ID NO 3
<211> LENGTH: 4
<212> TYPE: DNA
<213> ORGANISM: Artificial Sequence
<220> FEATURE:
<223> OTHER INFORMATION: Synthetic construct

<400> SEQUENCE: 3 aaaa                                                                4

<210> SEQ ID NO 4
<211> LENGTH: 4
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: n = uracil

<400> SEQUENCE: 4 ancg                                                                4

<210> SEQ ID NO 5
<211> LENGTH: 12
<212> TYPE: DNA
<213> ORGANISM: Artificial Sequence
<220> FEATURE:
<223> OTHER INFORMATION: Synthetic construct

<400> SEQUENCE: 5
cgcgaattcg cg                                                      12
```

```
<210> SEQ ID NO 6
<211> LENGTH: 19
<212> TYPE: DNA
<213> ORGANISM: Artificial Sequence
<220> FEATURE:
<223> OTHER INFORMATION: Synthetic construct

<400> SEQUENCE: 6
tttttttttt tttttttt                                                  19

<210> SEQ ID NO 7
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (19)..(19)
<223> OTHER INFORMATION: n = uracil

<400> SEQUENCE: 7
tttttttttt ttttttttn                                                 19
```